(12) United States Patent
Carballido Herrera et al.

(10) Patent No.: US 7,759,390 B2
(45) Date of Patent: Jul. 20, 2010

(54) INHIBITORS OF CCR9 ACTIVITY

(75) Inventors: Jose M. Carballido Herrera, Vienna (AT); Herbert Jaksche, Vienna (AT); Philipp Lehr, Vienna (AT); Gudrun Werner, Vienna (AT); Anthony Winiski, Vienna (AT)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/158,385

(22) PCT Filed: Dec. 22, 2006

(86) PCT No.: PCT/EP2006/012473

§ 371 (c)(1),
(2), (4) Date: Jun. 20, 2008

(87) PCT Pub. No.: WO2007/071440

PCT Pub. Date: Jun. 28, 2007

(65) Prior Publication Data

US 2008/0300295 A1 Dec. 4, 2008

(30) Foreign Application Priority Data

Dec. 22, 2005 (GB) ................... 0526255.5

(51) Int. Cl.
*A61K 31/38* (2006.01)
*C07D 333/32* (2006.01)

(52) U.S. Cl. ........................ 514/445; 549/65
(58) Field of Classification Search ............... 514/446, 514/445; 549/68, 79, 65
See application file for complete search history.

(56) References Cited

U.S. PATENT DOCUMENTS

2004/0038976 A1    2/2004   Fleming et al.

FOREIGN PATENT DOCUMENTS

| WO | 9729743 | 8/1997 |
|---|---|---|
| WO | 0128537 | 4/2001 |
| WO | 0228353 | 4/2002 |
| WO | 02100851 | 12/2002 |
| WO | 03044009 | 5/2003 |
| WO | 03/057225 A2 | 7/2003 |
| WO | 03059893 | 7/2003 |
| WO | 2004007472 | 1/2004 |
| WO | 2004011443 | 2/2004 |
| WO | 2004016221 | 2/2004 |
| WO | 2004022525 | 3/2004 |

OTHER PUBLICATIONS

Patani et. al. "Bioisosterism: A Rational Approach in Drug Design", Chem. Rev. 1996, 3147-3176.*
Hcaplus 1982:406774 (1981).*
Hcaplus 2004:193108, (2004).*
Hcaplus 2002:293390, "Modulaton of CCR4 function for disease therapy", Collins et. al., Apr. 18, 2002.*
Patani et. al., "Bioisosterism: A Rational Approach in Drug Design", Chem. Rev., 96, 1996, pp. 3147-3176.*
ISR mailed May 5, 2007 from the European Patent Office for related application PCT/EP2006/012473 with pulication.
El-Maghraby, A.A. et al. "Synthesis of some New Thiophene Derivatives of Antimicrobial Activity. Part II", Egyptian Journal of Pharmaceutical Science, Vo. 23, No. 4., 1982, pp. 327-336.
El-Naggar, et al., "Synthesis of Thiophen -2-Sulfonyl-Amino Acid and Dipeptide Derivatives," Egypt. J. Chem. 23, No. 4, pp. 273-279 (1980).

* cited by examiner

*Primary Examiner*—Janet L Andres
*Assistant Examiner*—Binta M Robinson
(74) *Attorney, Agent, or Firm*—John Alexander

(57) ABSTRACT

Compounds of formula I, wherein one of $R_1$ and $R_2$ is thienyl which is substituted by halogen and the other of $R_1$ and $R_2$ is substituted phenyl, wherein the substituents are as defined in the claims, with the proviso that the phenyl group is substituted by at least a cyano, carboxy or $(C_{1-4})$alkyloxycarbonyl group, are inhibitors of CCR9 activity and useful for therapeutic treatment.

(I)
$$R_1-\underset{H}{N}-\underset{\underset{O}{\|}}{\overset{\overset{O}{\|}}{S}}-R_2$$

4 Claims, No Drawings

INHIBITORS OF CCR9 ACTIVITY

The present invention relates to inhibitors of CCR9 activity.

This application is the National Stage of Application No. PCT/EP2006/012473, filed on Dec. 22, 2006, which claims benefit under 35 U.S.C. §119(a-d) of GB 0526255.5. The contents of both are incorporated herein by reference in their entirety.

CC chemokine ligand 25 (CCL25), originally described as thymus-expressed chemokine (TECK), plays a crucial role in T cell homing to the small intestine via signaling through CC chemokine receptor 9 (CCR9). CCL25 is constitutively expressed within the small intestine, especially in epithelial crypts, while being weakly or not all in the colon and at other mucosal surfaces. CCR9 is the only known receptor for TECK/CCL25. The expression of CCR9 strongly correlates with the ability of peripheral T lymphocytes to home to the small intestine. The majority of intestinal intraepithelial lymphocytes (IEL) and lamina propria T lymphocytes (LPL) are CCR9$^+$, whereas a much lower percentage of T cells circulating in blood are CCR9$^+$. The CCR9$^+$ T cells found in peripheral blood almost exclusively display the intestinal homing receptor $\alpha_4\beta_7$. Blocking CCR9 with antibody against TECK/CCL25 significantly inhibits homing of T lymphocytes to the small intestine. In addition, there is a strict localization of TECK/CCL25 and CCR9$^+$ LPL in the small rather than large intestine, suggesting a distinctive mechanism of lymphocyte recruitment in different segments of the gastrointestinal tract.

Studies have also suggested a role of TECK/CCL25 in T lymphocyte-endothelium interaction in inflamed intestinal mucosa. There is an increase of TECK/CCL25 expression and an enhanced LPL adhesion to the small intestinal mucosa after TNFα stimulation. Desensitization of CCR9 or anti-TECK/CCL25 could attenuate the recruitment of lymphocytes to the microvessels of small intestine. Thus, the targeted blockade of CCL25-CCR9 interactions may provide an effective therapeutic treatment in immune-mediated diseases, e.g. intestinal disorders, such as autoimmune and inflammatory diseases or conditions. T lymphocyte (T cell) infiltration into the small intestine and colon has been linked specifically to the pathogenesis of Coeliac diseases, food allergies, rheumatoid arthritis, human inflammatory bowel diseases (IBD) which include Crohn's disease and ulcerative colitis, e.g. including ulcerative proctitis. Disease which are also described to be mediated by CCR9 e.g. include allergic diseases, psoriasis, atopic dermatitis, asthma, fibrotic diseases, disorders and diseases originating or mediated by transplantation, e.g. graft rejection, and cancer, such as leukemia (acute lymphocytic leukemia), solid tumor, thymoma, thymic carcinoma.

Now compounds have been found which show surprising activity as CCR9 inhibitors.

In one aspect the present invention provides a compound of formula

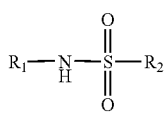

I wherein
one of $R_1$ and $R_2$ is thienyl which is substituted by halogen, and the other of $R_1$ and $R_2$ is phenyl, wherein phenyl is substituted by one or more alkyl, such as $(C_{1-6})$alkyl, e.g. methyl, tert.butyl,
haloalkyl, such as halo$(C_{1-4})$alkyl, e.g. $CF_3$,
alkoxy, such as $(C_{1-4})$alkoxy,
arylalkoxy, such as $(C_{6-12})$aryl$(C_{1-4})$, such as benzyloxy,
aryloxy, such as $(C_{6-12})$aryloxy, such as phenoxy,
haloalkoxy, such as halo$(C_{1-4})$alkoxy, e.g. $OCF_3$,
alkoxycarbonyl, such as $(C_{1-4})$alkoxycarbonyl, e.g. methoxycarbonyl,
carboxy,
cyano,
halogen, e.g. fluoro, chloro, bromo,
e.g. with the proviso, that phenyl is substituted by at least cyano, carboxy or alkyloxyarbonyl, e.g. $(C_{1-4})$alkyloxycarbonyl, such as methoxycarbonyl, e.g. phenyl is substituted by cyano.

Thienyl includes thien-2-yl, thien-3-yl.

In another aspect the present invention provides a compound of formula I, wherein one of $R_1$ and $R_2$ is halogenated thienyl and the other of $R_1$ and $R_2$ is phenyl wherein $R_1$ and $R_2$ independently of each other are
  (methyl)(cyano)phenyl, e.g. 2-methyl-4-cyanophenyl,
  (trifluoromethoxy)(cyano)phenyl, e.g. 2-trifluoromethoxy-4-cyanophenyl,
  (chloro)(cyano)phenyl, e.g. 2-cyano-5-chlorophenyl, 3-chloro-4-cyanophenyl,
  chlorothienyl, e.g. including dichlorothienyl, e.g. 5-chlorothien-2-yl, 4,5-dichlorothien-2-yl, 2,5-dichlorothien-3-yl,
  (chloro)(bromo)thienyl, e.g. including (dichloro)(bromo)thienyl, such as 2,5-dichloro-4-bromo-thien-3-yl.

Preferably $R_1$ is phenyl. Preferably $R_2$ is halogenated thienyl. Preferably phenyl is substituted as defined above and thienyl is substituted by halogen, e.g. including F, Cl, Br, such as Cl, Br.

In another aspect the present invention provides a compound of formula I, wherein $R_1$ is
  (methyl)(cyano)phenyl, e.g. 2-methyl4-cyanophenyl,
  (trifluoromethoxy)(cyano)phenyl, e.g. 2-trifluoromethoxy-4-cyanophenyl,
  (chloro)(cyano)phenyl, e.g. 2-cyano-5-chlorophenyl, 3-chloro-4-cyanophenyl, and
$R_2$ is
  chlorothienyl, e.g. including dichlorothienyl, e.g. 5-chlorothien-2-yl, 4,5-dichlorothien-2-yl, 2,5-dichlorothien-3-yl,
  (chloro)(bromo)thienyl, e.g. including (dichloro)(bromo)thienyl, such as 2,5-dichloro-4-bromo-thien-3-yl.

In a compound of formula I each single defined substituent may be a preferred substituent, e.g. independently of each other substituent defined.

In another aspect the present invention provides a compound selected from the group consisting of
1. 5-Chloro-thiophene-2-sulfonic acid (4-cyano-2-methyl-phenyl)-amide,
2. 4,5-Dichloro-thiophene-2-sulfonic acid (5-chloro-2-cyano-phenyl)-amide,
3. 4,5-Dichloro-thiophene-2-sulfonic acid (4-cyano-2-trifluoromethoxy-phenyl)-amide,
4. 4,5-Dichloro-thiophene-2-sulfonic acid (3-chloro-4-cyano-phenyl)-amide,
5. 5-Chloro-thiophene-2-sulfonic acid (5-chloro-2-cyano-phenyl)-amide,
6. 4-Bromo-2,5-dichloro-thiophene-3-sulfonic acid (4-cyano-2-trifluoromethoxy-phenyl)-amide,
7. 4-Bromo-2,5-dichloro-thiophene-3-sulfonic acid (5-chloro-2-cyano-phenyl)-amide, 8. 5-Chloro-thiophene-2-sulfonic acid (4-cyano-2-trifluoromethoxy-phenyl)-amide,
9. 2,5-Dichloro-thiophene-3-sulfonic acid (4-cyano-2-trifluoromethoxy-phenyl)-amide, and
10. 2,5-Dichloro-thiophene-3-sulfonic acid (5-chloro-2-cyano-phenyl)-amide.

In another aspect the present invention provides an N-(cyano-phenyl)-halothienyl-sulfonamide, e.g. wherein halothienyl is thienyl substituted by halogen, e.g. one or morefold.

Compounds provided by the present invention are hereinafter designated as "compound(s) of (according to) the present invention". A compound of the present invention includes a compound in any form, e.g. in free form, in the form of a salt, in the form of a solvate and in the form of a salt and a solvate.

In another aspect the present invention provides a compound of the present invention in the form of a salt.

Such salts include preferably pharmaceutically acceptable salts, although pharmaceutically unacceptable salts are included, e.g. for preparation/isolation/purification purposes.

The present invention includes a compound of the present invention in any isomeric form and in any isomeric mixture. The present invention also includes tautomers of a compound provided by the present invention, where tautomers can exist.

In another aspect the present invention provides a process for the production of a compound of formula I comprising the steps of a. reacting a compound of formula

$$R_1\text{—}NH_2 \qquad\qquad II$$

wherein $R_1$ is as defined above,
with a compound of formula

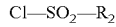
$$Cl\text{—}SO_2\text{—}R_2 \qquad\qquad III$$

wherein $R_2$ is as defined above,
and b) isolating a compound of formula I obtained from the reaction mixture.

In an intermediate of formula II or of formula III (starting materials), functional groups, if present, optionally may be in protected form or in the form of a salt, if a salt-forming group is present. Protecting groups, optionally present, may be removed at an appropriate stage, e.g. according, e.g. analogously, to a method as conventional.

A compound of the present invention thus obtained may be converted into another compound of the present invention, e.g. a compound of the present invention obtained in free form may be converted into a salt of a compound of the present invention and vice versa.

The above reaction is a an amine sulfonylation reaction and may be carried out as appropriate, e.g. analogously to a method as convential, or as described herein. Intermediates (starting materials) of formula II and of formula III are known or may be prepared according, e.g. analogously, to a method as conventional or as described herein. Any compound described herein, e.g. a compound of the present invention and intermediates of formula II and III may be prepared as appropriate, e.g. according, e.g. analogously, to a method as conventional, e.g. or as specified herein. N-(cyano-phenyl)-thienylsulfoamides may be e.g. obtained by reacting a cyanoaniline with a thienyl-sulfonylchloride.

E.g., in case that phenyl in a compound of formula I is substituted by carboxy, protection of said carboxy group in a compound of formula II, e.g. by esterification to obtain a corresponding alkoxycarbonyl derivative, may be an option. The compound of formula II wherein aryl is substituted by alkylcarbonyloxy may be reacted with a compound of formula III to obtain a compound of formula I wherein aryl is substituted by alkoxycarbonyl and the carboxylic acid ester thus obtained may be saponified to obtain a corresponding compound of formula I wherein aryl is substituted by carboxy.

The compounds of the present invention, e.g. including a compound of formula I, exhibit pharmacological activity and are therefore useful as pharmaceuticals. Compounds of the present invention show dose-dependent inhibition in the Scintillation proximity assay (SPA ASSAY)
Eu-GTP-BINDING ASSAY
Calcium Mobilization Assay (FLIPR ASSAY)

e.g. under conditions as convential, e.g. under conditions as described herein, e.g. in the $IC_{50}$ nanomolar up to the low micromolar range.

Activity in inflammatory bowel disease treatment is e.g. determined in a SCID mouse model of inflammatory bowel disease.

Scintillation Proximity ASSAY (SPA)

The Principle of SPA

Chemokines mediate their actions through seven transmembrane spanning G protein coupled receptors (GPCR) on the target cells. Ligand binding to GPCRs stimulates the GTP/GDP exchange at the heterotrimeric G proteins, composed of α, β, and γ subunits. The agonist-bound GPCR initiates the guanine nucleotide cycle by catalyzing dissociation of GDP from the α-subunit, allowing the binding of endogenous GTP, and the dissociation of the βγ complex. The Gα-GTP and Gβγ subunits can each activate effectors such as adenylyl cyclase, phospholipase C and ion channels (see e.g. Neer E J, Cell; 80:249-57 (1995)). The Gα-GTP is inactivated by an intrinsic GTPase activity, which hydrolyzes GTP to GDP; subsequently the GDP-containing G protein is ready for the next activation cycle. This process can be monitored in vitro by measuring the binding of hydrolysis-resistant GTP analogues, such as 5'-O-(3-[$^{35}$S]thiophosphate ([$^{35}$S]-GTPγS), to cell membranes containing the receptor of interest. A GTPγS scintillation proximity assay (SPA) is shown to be a useful functional assay to monitor the activation of CCR9 by TECK.

SPA is a homogeneous and versatile assay technology for the rapid and sensitive assay of a wide range of biological processes. The assay format requires no separation steps and is amenable to automation. The membranes bearing the receptor are coupled via the glycoprotein moiety to the fluorescent wheat germ agglutinin coated beads(Amersham Bioscience, #RNPQ 0001). Once immobilized, the receptor is close enough to the bead so that, if the agonist-bound GPCR initiates the guanine nucleotide cycle, [$^{35}$S]GTPγS (Amersham Bioscience, #SJ1308) binds to the membrane. The radioactive molecule will be held in close enough proximity so that the decay particles stimulate the scintillant within the bead to emit light which is then detected by a PMT-based scintillation counter. Unbound radioligand is too distant from the bead to transfer energy and therefore goes undetected.

Cells and Cell Culture

Mouse pre-B-cells 300-19 transfected with human CCR9 receptor are grown in suspension in cell culture flasks (100-ml cell suspension in 162 cm² cell culture flask) at 37° C. in a humidified atmosphere containing 5% CO2 in RPMI 1640 medium supplemented with penicillin (100 IU/ml), streptomycin (0.1 mg/ml), L-glutamine (to 4.5 mM final conc.), 10% FBS, 1 mM sodium pyruvate, 0.05 μM 2-mercaptoethanol, 1.5 μg/ml puromycin and 20 mM HEPES. Cells are usable for ~12 passages for membrane preparation (i.e. CCR9 receptor density is acceptably high enough). Expression of CCR9 is monitored by FACS analysis using Alexa Fluor 647-conjugated mouse anti-human CCR9 antibody. The CCR9 expression should be no less than 50% positive cells via FACS relative to the Alexa Fluor isotype control. As an approximation, one can split a culture of $10 \times 10^5$ cells/ml using a 1:30-1:50 dilution, and reach the starting cell density after 2-3 days (~4-5 days for a spinner flask culture). Cells are harvested at a density of $8\text{-}10 \times 10^5$ cells/ml by centrifugation at 300-1000 g for 10 minutes. Generally, the cells are cultured and expanded to result in approximately $1 \times 10^8$ cells. The combined cell pellet is washed once in cold PBS (without calcium and magnesium), resuspended via pipetting in cold membrane buffer at approximately $2 \times 10^8$ cells/ml, frozen on dry ice, and stored at $-80°$ C.

Membrane Buffer

Membrane buffer pH=7.5 (1000 ml): 7.5 mM Tris, 12.5 mM $MgCl_2$, 0.3 mM EDTA, 1 mM EGTA, 250 mM Sucrose, sterile-filtered and stored at +4° C.

Homogenization Buffer (50 ml):

Membrane buffer 45 ml+10% glycerol

Preparation of Membranes

Pipette the cell suspension solution into sturdy tubes and homogenize each solution. Transfer the homogenates to centrifuge tubes and centrifuge 10 minutes at 1000 g. Collect supernatants. Add 20 ml of new membrane buffer to each pellet, transfer into the original sturdy tubes and homogenize and centrifuge once more. Collect the supernants. Centrifuge the combined supernatants at 40000 g for 30 minutes. Resuspend each pellet in 3 ml of cold homogenization buffer with a Dounce homogenizer. Determine protein concentration in the homogeneous suspension (BIO RAD assay, reference BSA). Bradford method (Microassay Procedure). As an approximation, $1 \times 10^{10}$ cells results in a membrane yield of 10-20 mg protein. Store aliquots at $-80°$ C.

Optimized Buffers and Solutions for Compound Testing

HEPES/BSA buffer: 50 mM HEPES (pH 7.4), 50 µg/ml BSA 2.5× Assay buffer: 50 mM HEPES pH 7.4, 50 µg/ml BSA, 25 mM $MgCl_2$, 25 µM GDP, 250 mM NaCl, 375 µg/ml saponin TECK: Dilutions of TECK is prepared with 0.1% BSA in PBS to yield 20-fold TECK solution for the GTP binding assay. For compound testing, a concentration of 7.4 µM TECK is used to give a final concentration of 0.37 µM in the reaction.

Compound dilution: Test compounds are dissolved in DMSO at 100-fold the highest, final concentration in the assay. Serial dilutions of these concentrated compound solutions are made in DMSO, which are diluted 5-fold into HEPES/BSA buffer to generate 20×-concentrated compound solutions containing a DMSO concentration of 20% (v/v). The final concentration of DMSO in assays is 1% (v/v).

Membrane dilution: Before use, membranes (2.4 mg/ml stock; batch CCR9-1) are diluted in HEPES/BSA buffer to give 60 µg/ml. 50 µl of this membrane are added to each well. (3 µg/well final assay concentration for membrane batch CCR9-1).

Final assay condition for compound testing: 50 mM HEPES pH 7.4, 50 µg/ml BSA, 100 mM NaCl, 10 mM $MgCl_2$, 10 µM GDP, 150 µg/ml Saponin, 0.37 µM TECK and 3 µg/well membrane.

Assay Protocol

The assay is performed in the time zero format, which involves the sequential addition of test samples, membrane, radio-ligand and beads as separate additions without any preincubation.

Briefly, membranes are incubated in the presence of agonist and compound with [$^{35}$S]GTPγS and scintillation beads for 1 hour at room temperature on a vibrating mixer. Using a liquid handling robot the following reagents are dispatched into a 96 well White&Clear Isoplate (Wallac, #1450-515) in the following sequence:

40 µassay buffer (20 mM HEPES pH 7.5, 100 mM NaCl, 10 mM $MgCl_2$, 1µ MGDP, 10 µg/ml Saponin, 50 µg/ml BSA).

10 µl agonist Human TECK/CCL25, 25 µg/ml (R&D Systems, #334-TK-025)

10 µl sample in 50% DMSO

50 µl membranes, 60 µg/ml in assay buffer

50 µl [$^{35}$S]GTPγS, 1 nM in assay buffer

40 µl bead suspension 18.75 mg/ml assay buffer.

After incubation plates are centrifuged for 5 minutes at 1000×g and counted in the MicroBeta Counter (EG&G Wallac) in ParaLux SPA counting mode.

Data Analysis

Data analysis is performed with Excel fit 4.0 software package (Microsoft). In order to determine the quality of the experimental window of the assay, the Z'-factor is calculated using only control data (basal values and stimulated values). For this assay Z' is estimated with 0.73 which indicates a large separation band and an overall excellent assay quality.

Eu-GTP BINDING ASSAY

The Principle of the Eu-GTP BINDING ASSAY

A time-resolved fluorometric method to measure G-protein activation which uses a non-radioactive, non-hydrolyzable europium-labeled GTP analog, Eu-GTP.

Materials

RPMI 1640 Medium with (made from powder, Gibco #074-01800)

Penicillin/Streptomycin Solution, liquid (Gibco #15140-122)

FBS (certified, obtained from Gibco [#16000] and then heat inactivated)

Sodium pyruvate (Gibco #11360-039)

Puromycin (used as selection marker; Sigma #P-8833)

Complete protease inhibitor (Roche #1697498)

Alexa Fluor 647-conjugated mouse anti-human CCR9 antibody (Pharmingen #557975)

Alexa Fluor 647-conjugated $IgG2_a$ Isotype control (BD Pharmingen #557715)

TECK (aa24-150-his6, BMP Tool Protein Data base #BTP04-005213, Aliquots of TECK stock solution (5 mg/ml; ~350 µM) stored at $-80°$ C.

BSA (Roche Diagnostics GmbH #775827)

Eu-GTP (Perkin-Elmer Life Sciences, Wallac, Turku, Finland; product code: AD0260) kit contains the following components:

Eu-GTP (1.65 nmol) The lyophilized Eu-GTP was reconstituted with distilled water to yield a Eu-GTP concentration of 10 µM. Aliquots of the reconstituted Eu-GTP were stored at $-20°$ C.

GDP (2.3 µmol)

The lyophilized GDP is reconstituted with distilled water to yield a GDP concentration of 2 mM. Aliquots of the reconstituted GDP are stored at $-20°$ C.

VICTOR²™ V Multilabel Counter (Perkin-Elmer Life Sciences, Wallac, Turku, Finland) MultiScreen Vacuum Manifold (Millipore #MAVM 096OR)

Cells and Cell Culture

To be carried out as described herein under "Cells and cell culture" in the "Scintillation proximity assay (SPA)"

Membrane Buffer and Homogenization Buffer

To be carried out as described herein under "Membrane buffer and Homogenization buffer" in the "Scintillation proximity assay (SPA)"

Preparation of Membranes

To be carried out as described herein under "Preparation of membranes" in the "Scintillation proximity assay (SPA)"

Optimized Buffers and Solutions for Compound Testing

To be carried out as described herein under "Optimized buffers and solutions for compound testing" in the "Scintillation proximity assay (SPA)"

For Eu-GTP: Dilute Eu-GTP stock solution to 100 nM in HEPES/BSA buffer before use. GTP wash solution: The 10×GTP wash solution is diluted 1:10 with distilled water and cooled on ice.

Eu-GTP Binding Assay Protocol for Compound Testing

The Eu-GTP binding assay is performed in a final volume of 100 µl in Acro-Well filter plates.

Assay components are added into the wells in the following order:

Add 40 µl assay buffer (2.5×) to each well (Wells B2 to G12). Add 5 µl TECK (7.4 µM) to wells of columns 2-11 and the final concentration of TECK in the assay is 0.37 µM. Add 5 µl of 0.1% BSA to wells of column 12, which serve as the basal control. Add 5 µl of each compound concentration (20-fold of the final concentration in 20% DMSO) in triplicate to columns 3-11 (i.e. 3 wells per concentration). Add 5 µl of 20% DMSO into wells of column 2 and 12, which are the stimulated and basal controls, respectively. The final DMSO concentration in all wells is 1% (v/v). Add 50 µl membranes (3 µg/sample) into all wells and mix shortly at 800 rpm on a microtiter plate shaker (MS1 Minishaker). The plate is incubated for 30-min with slow shaking at 300 rpm on an orbital plate shaker (MTS 2/4 digital microtiter shaker). Add 10 µl of the 100 nM Eu-GTP per well to yield a final concentration of 10 nM. The plate is incubated for another 30-min with slow shaking at 300 rpm on the orbital plate shaker. The reaction is terminated by vacuum filtration and the filter plate is washed two times via vacuum filtration with 300 µg of ice-cold GTP wash buffer per well. Eu-GTP retained on the filter is measured with a VICTOR²™ V Multilabel Counter (340 nm excitation/615 nm emission, 0.4 ms delay, 0.4 ms window) within 30 min after the wash step.

Data Analysis

The actual Eu-GTP binding signal caused by agonist stimulation (=a) is compared to basal binding (=b) and the final result is calculated as a percentage over basal binding [percent over basal=(a/b×100)−100].

The dose-response curves for the calculated percent stimulation above basal binding for each test compound are fitted using the Excel add-on program XLfit™ (ID Business Solutions, Guilford, Surrey, UK) to the 4-parameter logistic equation (Model 205):

$$y = A + ((B-A)/(1+((C/x)^D)))$$

wherein x is concentration values, y percent stimulation above basal binding corresponding to the x values.

The fitted parameters are:

A: bottom plateau of the curve, B: top plateau of the curve, C: x value at the middle of the curve (i.e. between top and bottom plateaus), D: slope factor (also known as the Hill coefficient).

The $IC_{50}$ for the assay is defined as the midway point between the solvent control containing TECK and the solvent control without stimulus.

The Z' value is calculated using only control data (6 basal values and 6 stimulated values) for each experiment. The Z' varies between 0.56 and 0.79 in all assays.

In another aspect the present invention provides the use of the SPA assay or the use of the Eu-GTP BINDING ASSAY in method for the identification of CCR9 inhibitors.

The SPA and the Eu-GTP BINDING ASSAY are used as described herein. CCR9 inhibitors which may be identified by use of these assay include antibodies and chemical compounds, e.g. low molecular weight compounds.

Calcium Mobilization ASSAY a) The Principle of Calcium Mobilization Assay

Chemokine receptors are pertussis toxin (PTX)-sensitive Gαi protein-coupled seven-transmembrane receptors. A number of studies have demonstrated the activation of various signaling pathways for most chemokines and in multiple cell types, including elevation of cytosolic intracellular calcium concentration ($[Ca^{2+}]_i$). This process can be monitored in vitro by measuring ($[Ca^{2+}]_i$ levels via calcium-sensitive fluorescent dyes using a fluorometric imaging plate reader (FLIPR). Intracellular calcium mobilization in MOLT-4 cells, as measured using the FLIPR technology, is shown to be a useful functional assay to monitor the activation of CCR9 by TECK.

b) Cells and Cell Culture

The human T cell leukemia line MOLT-4 was obtained from the American Type Culture Collection (ATCC, Manas-

TABLE A (Plate Layout)

| | 1 | 2 stimulated control | 3 Conc. 1 | 4 Conc. 2 | 5 Conc. 3 | 6 Conc. 4 | 7 Conc. 5 | 8 Conc. 6 | 9 Conc. 7 | 10 Conc. 8 | 11 Conc. 9 | 12 basal control |
|---|---|---|---|---|---|---|---|---|---|---|---|---|
| A | 1 | | | | | | | | | | | |
| B | | DMSO | Cmpd 1 | Cmpd 1 | Cmpd 1 | Cmpd 1 | Cmpd 1 | Cmpd 1 | Cmpd 1 | Cmpd 1 | Cmpd 1 | DMSO |
| C | | DMSO | Cmpd 1 | Cmpd 1 | Cmpd 1 | Cmpd 1 | Cmpd 1 | Cmpd 1 | Cmpd 1 | Cmpd 1 | Cmpd 1 | DMSO |
| D | | DMSO | Cmpd 1 | Cmpd 1 | Cmpd 1 | Cmpd 1 | Cmpd 1 | Cmpd 1 | Cmpd 1 | Cmpd 1 | Cmpd 1 | DMSO |
| E | | DMSO | Cmpd 2 | Cmpd 2 | Cmpd 2 | Cmpd 2 | Cmpd 2 | Cmpd 2 | Cmpd 2 | Cmpd 2 | Cmpd 2 | DMSO |
| F | | DMSO | Cmpd 2 | Cmpd 2 | Cmpd 2 | Cmpd 2 | Cmpd 2 | Cmpd 2 | Cmpd 2 | Cmpd 2 | Cmpd 2 | DMSO |
| G | | DMSO | Cmpd 2 | Cmpd 2 | Cmpd 2 | Cmpd 2 | Cmpd 2 | Cmpd 2 | Cmpd 2 | Cmpd 2 | Cmpd 2 | DMSO |
| H | | | | | | | | | | | | | sas, Va.). MOLT-4 cells are cultured in medium, which is RPMI-1640 supplemented with 10% FCS, 2 mM L-glutamine, 100 U/ml penicillin and 100 µg/ml streptomycin at 37° C. with 5% $CO_2$. Human serum albumin (HSA) is obtained from ZLB Behring (Vienna, Austria) as a 20% solution.

c) Calcium Mobilization Assay Protocol

The following solutions are prepared:
HPSS: 7.01 g NaCl, 0.4 g KCl, 0.2 g $MgSO_4.7 H_2O$, 4.76 g HEPES, 2 g Glucose. $H_2O$ (in 1 L)
Work Buffer (WB): 600 ml HPSS+0.9 ml 1 M $CaCl_2$+12 ml 1 M HEPES.
% BSA/WB: 60 ml WB+0.06 g Bovine Serum Albumin (BSA; Sigma A7906).
Probenicid Stock Solution: 356 mg Probenicid+2.5 ml 1 N NaOH+2.5 ml WB.
Probenicid buffer: 350 ml WB+3.5 ml Probenicid stock solution.
Fluo-4 solution: 50 µg Fluo-4, AM+0.025 ml DMSO+0.025 ml Pluronic F-127 (Invitrogen/Molecular Probes #P3000MP; supplied as 20% in DMSO).
Dye solution: 105 ml medium+1.05 ml Probenicid stock solution+2.1 ml of 1 M HEPES+0.21 ml Fluo-4 solution.
TECK: prepared in 0.1% BSA/WB MOLT4 cells are harvested and loaded with Fluo-4/acetoxymethyl ester (Fluo-4/AM) according to manufacturer's instructions (Invitrogen/Molecular Probes, Eugene, Oreg.). Briefly, cells are incubated ($1\times10^7$ cells per 3 ml) in dye solution for 60 min at 37° C. and 5% $CO_2$. Subsequently, cells are washed twice with Probenicid buffer and pipetted into 96-well assay plates (clear-bottomed, black polystyrene plates; Corning Costar #3603) at $2\times10^5$ cells and 0.075 ml pro well and then centrifuged at 1200 revolutions per minute for 3-4 min to evenly distribute the cells at the bottom of the plates. The plates are incubated for 60 min in the dark at room temperature (RT) to allow de-esterification of intracellular AM esters. Test compounds are first dissolved in DMSO, and 0.006 ml of these DMSO stock solutions are diluted into 0.194 ml WB (±HSA) before injection into the cell plates (0.025 ml/well). After a 30-min incubation in the dark at RT, intracellular $Ca^{2+}$ mobilization is monitored after injection of TECK (to give a near maximal effective concentration of at least $EC_{80}$) using a FLIPR instrument (Molecular Devices, Ismaning/Munich, Germany). Baseline readings are collected (at 3.5-sec intervals) for 25 sec before injection of TECK (0.025 ml/well) followed by 1-sec intervals for the 80 sec after TECK injection. Fluorescence readings are performed using standard settings, and all data are normalized using the formula:

d) Calculation

Calcium response=[Fmax−Fmin]/Fmin where Fmax represents the maximal fluorescence response and Fmin the minimal, base line, fluorescence. The dose-response curves for the calcium response data for each test compound are fitted using the Excel add-on program XLfit™ (ID Business Solutions, Guilford, Surrey, UK) to the 4-parameter logistic equation (Model 205) to determine $IC_{50}$ values.

The compounds of the present invention show activity in assays as described herein and a compound of the present invention is prone to show therapeutic activity in the treatment of disorders which are mediated by CCR9 activity.

Disorders which are mediated by CCR9 activity and which are prone to be successfully treated with an CCR9 inhibitor, e.g. include disorders wherein the activity of CCR9 plays a causal or contributory role, such as disorders associated with the binding of CCR9 to CCL25, e.g. disorders mediated by CCR9-mediated homing of leukocytes in a subject.

Disorders as used herein include diseases.

Disorders which are prone to be mediated by CCR9 activity e.g. include
disorders associated with inflammation
e.g. including (chronic) inflammatory disorders, disorders related with the inflammation of the bronchi, e.g. including bronchitis, cervix, e.g. including cervicitis, conjunctiva, e.g. conjunctivitis, esophagus, e.g. esophagitis, heart muscle, e.g. myocarditis, rectum, e.g. proctitis, sclera, e.g. scleritis, gums, involving bone, pulmonary inflammation (alveolitis), airways, e.g. asthma, such as bronchial asthma, acute respiratory distress syndrome (ARDS), inflammatory skin disorders such as contact hypersensitivity, atopic dermatitis; fibrotic disease (e.g., pulmonary fibrosis), encephilitis, inflammatory osteolysis,
disorders associated with conditions of the immune system,
immune, such as autoimmune disorders e.g. including Graves' disease, Hashimoto's disease (chronic thyroiditis), multiple sclerosis, rheumatoid arthritis, arthritis, gout, osteoarthritis, scleroderma, lupus syndromes, systemic lupus erytomatosis, Sjoegren's syndrome, psoriasis, inflammatory bowel disease, including Crohn's disease, colitis, e.g. ulcerative colitis; sepsis, septic shock, autoimmune hemolytic anemia (AHA), autoantibody triggered urticaria, pemphigus, nephritis, glomerulonephritis, Goodpastur syndrom, ankylosing spondylitis, Reiter's syndrome, polymyositis, dermatomyositis, cytokine-mediated toxicity, interleukin-2 toxicity, alopecia areata, uveitis, lichen planus, bullous pemphigoid, myasthenia gravis, type I diabetes mellitus, immune-mediated infertility such as premature ovarian failure, polyglandular failure, hypothyroidism, pemphigus vulgaris, pemphigus I-oliaceus, paraneoplastic pemphigus, autoimnune hepatitis including that associated with hepatitis B virus (HBV) and hepatitis C virus (HCV), Addison's disease, autoimmune skin diseases, such as psoriasis, dermatitis herpetiformis, epidermolysis bullosa, linear IgA bullous dermatosis, epidermolysis bullosa acquisita, chronic bullous disease of childhood, pernicious anemia, hemolytic anemia, vitiligo, type I, type II and type III autoimmune polyglandular syndromes, Autoimmune Hypoparathyroidism, Autoimmune Hypophysitis, Autoimmune Oophoritis, Autoimmune Orchitis, pemphigoid gestationis, cicatricial pemphigoid, mixed essential cryoglobulinemia, immune thrombocytopenic purpura, Goodpasture's syndrome, autoimmune neutropenia, Eaton-Lambert myasthenic syndrome, stiff-man syndrome, encephalomyelitis, acute disseminated encephalomyelitis, Guillain-Barre syndrome, cerebellar degeneration, retinopathy, primary biliary sclerosis, sclerosing cholangitis autoimmune hepatitis, gluten-sensitive enteropathy, reactive arthritides, polymyositis/dermatomyositis, mixed connective tissue disease, Bechet's syndrome, polyarteritis nodosa allergic anguitis and granulomatosis (Churg-Strauss disease), polyangiitis overlap syndrome (hypersensitivity) vasculitis, Wegener's granulomatosis, temporal arteritis Kawasaki's disease, sarcoidosis, cryopathies, Celiac disease,
disorders associated with cytokine-mediated toxicity,
e.g. including interleukin-2 toxicity,
disorders associated with the bone,
e.g. including osteoporosis, osteoarthritis, disorders associated with the brain and the nerves,
neurodegenerative disorders, e.g. including disorders of the central nervous system as well as disorders of the peripheral nervous system, e.g. CNS disorders including central nervous infections, brain injuries, cerebrovascular disorders and their consequences, Parkinson's disease, corticobasal degeneration, motor neuron disease, dementia including ALS, multiple sclerosis, traumatic disorders, including trauma and inflammatory consequences of trauma, traumatic brain injury, stroke, post-stroke, post-traumatic brain injury,
small-vessel cerebrovascular disease, eating disorders; further dementias, e.g. including Alzheimer's disease, vascular dementia, dementia with Lewy-bodies, frontotemporal dementia and Parkinsonism linked to chromosome 17, frontotemporal dementias, including Pick's disease, progressive nuclear palsy, corticobasal degeneration, Huntington's disease, thalamic degeneration, Creutzfeld Jakob dementia, HIV dementia, schizophrenia with dementia, Korsakoff's psychosis,
cognitive-related disorders, such as mild cognitive impairment, age associated memory impairment, age-related cognitive decline, vascular cognitive impairment, attention deficit disorders, attention deficit hyperactivity disorders, and memory disturbances in children with learning disabilities; conditions associated with the hypothalamic-pituitary-adrenal axis,
neuronal disorders, e.g. including neuronal migration disorders, hypotonia (reduced muscle tone), muscle weakness, seizures, developmental delay (physical or mental development difficulty), mental retardation, growth failure, feeding difficulties, lymphedema, microcephaly, symptoms affecting the head and the brain, motor dysfunction;
disorders associated with the eye,
e.g. including uveoritinitis, vitreoretinopathy, corneal disease, iritis, iridocyclitis, cateracts, uveitis, diabetic retinopathy, retinitis pigmentosa, conjunctivits, keratitis,
disorders associated with the gastrointestinal tract
e.g. including colitis, inflammatory bowel disease, Crohn's disease, ulcerative colitis, peptic ulceration, gastritis, oseophagitis,
disorders associated with the heart and vascular conditions
e.g. including cardiovascular disorders, e.g. including cardiac failure, cardiac infarction, cardiac hypertrophy, heart failure, e.g. including all forms of heart pumping failures such as high-output and low-output, acute and chronic, right sided or left-sided, systolic or diastolic, independent of the underlying cause; myocardial infarction (MI), MI prophylaxis (primary and secondary prevention), acute treatment of MI, prevention of complications; heart disorders, proliferative vascular disorders, vasculitides, polyarteritis nodosa, inflammatory consequences of ischemia, ischemic heart disease, myocardial infarction, stroke, peripheral vascular disease, pulmonary hypertension,
ischemic disorders, e.g. including myocardial ischemia, e.g. stable angina, unstable angina, angina pectoris, bronchitis; asymptomatic arrhythmias such as all forms of atrial and ventricular tachyarrhythmias, atrial tachycardia, atrial flutter, atrial fibrillation, atrio-ventricular reentrant tachycardia, preexitation syndrome, ventricular tachycardia, ventricular flutter, ventricular fibrillation, bradycardic forms of arrhythmias; arrhythmia, chronic obstructive pulmonary disease,
hypertension, such as systolic or diastolic high blood pressure, e.g. essential and secondary hypertension, e.g. including hypertensive vascular disorders, such as primary as well as all kinds of secondary arterial hypertension, renal, endocrine, neurogenic and others;
peripheral vascular disorders in which arterial and/or venous flow is reduced resulting in an imbalance between blood supply and tissue oxygen demand, e.g. including artherosclerosis, chronic peripheral arterial occlusive disease (PAOD), acute arterial thrombosis and embolism, inflammatory vascular disorders, Raynaud's phenomenon and venous disorders; atherosclerosis, a disease in which the vessel wall is remodeled, e.g. including accumulation of cells, both smooth muscle cells and monocyte/macrophage inflammatory cells, in the intima of the vessel wall;
hypotension,
disorders associated with the liver and the kidneys,
e.g. including renal disorders, kidney disorders, e.g. acute kidney failure, acute renal disease, liver disorders, e.g. cirrhosis, hepatitis, liver failure, cholestasis, acute/chronic hepatitis, sclerosing cholangitis, primary biliary cirrhosis, acute/chronic interstitial/glomerulonephritis, granulomatous diseases,
disorders associated with stomach or pancreas conditions
e.g. including stomach disorders, e.g. gastric ulcer, gastrointestinal ulcer, pancreatic disorders, pancreatic fatigue,
disorders associated with the respiratory tract and lung
e.g. including pulmonary disorders, chronic pulmonary disease, acute (adult) respiratory distress syndrome (ARDS), asthma, asthma bronchitis, bronchiectasis, diffuse interstitial lung disorders, pneumoconioses, fibrosing aveolitis, lung fibrosis,
disorders associated with skin and connective tissue conditions
e.g. including eczema, atopic dermatitis, contact dermatitis, psoriasis, acne, dermatomyositis, Sjörgen's syndrome, Churg-Struass syndrome, sunburn, skin cancer, wound healing, urticaria, toxic epidermal necrolysis,
disorders associated with allergic conditions,
e.g. including delayed-type hypersensitivity, allergic conjunctivitis, drug allergies, rhinitis, allergic rhinitis, vasculitis, contact dermatits;
disorders associated with angiogenesis,
e.g. including unsufficient ability to recruit blood supply, disorders characterised by odified angiogenesis, tumor associated angiogenesis,
disorders associated with cancer and cell overproliferation,
e.g. including premalignant conditions, hyperproliferative disorders, cancers whether primary or metastatic, cervical and metastatic cancer, cancer originating from uncontrolled cellular proliferation, solid tumors, such as such as described in WO02066019, including nonsmall cell lung cancer, cervical cancer; tumor growth, lymphoma, B-cell or T-cell lymphoma, benign tumors, benign dysproliferative disorders, renal carcinoma, esophageal cancer, stomach cancer, renal carcinoma, bladder cancer, breast cancer, colon cancer, lung cancer, melanoma, nasopharyngeal cancer, osteocarcinoma, ovarian cancer, uterine cancer; prostate cancer, skin cancer, leukemia, tumor neovascularization, angiomas, myelodysplastic disorders, unresponsiveness to normal death-inducing signals (immortalization), increased cellular motility and invasiveness, genetic instability, dysregulated gene expression, (neuro)endocrine cancer (carcinoids), blood cancer, lymphocytic leukemias, neuroblastoma; soft tissue cancer, prevention of metastasis,
disorders associated with diabetic conditions, e.g. including diabetes (type I diabetes, type II diabetes), diabetic retiropathy, insulin-dependent diabetes, diabetes mellitus, gestational diabetes), insulin hyposecretion, obesity;

disorders associated with endiometriosis, testicular dysfunctions, disorders associated with infectious disorders, e.g. with chronic infectous conditions, e.g. including bacterial disorders, otitis media, Lyme disease, thryoditis, viral disorders, parasitic disorders, fungal disorders, malaria, e.g. malaria anemia, sepsis, severe sepsis, septic shock, e.g. endotoxin-induced septic shock, exotoxin-induced toxic shock, infective (true septic) shock, septic shock caused by Gram-negative bacteria, pelvic inflammatory disease, AIDS, enteritis, pneumonia; meningitis, encephalitis, lymphatic filarial infection, disorders associated with myasthenia gravis, disorders associated with nephritis, e.g. including glomerulonephritis, interstitial nephritis, Wegener's granulomatosis, fibrosis, disorders associated with pain, e.g. associated with CNS disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation);

non-central neuropathic pain, e.g. including that associated with post mastectomy pain, phantom feeling, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia;

pain associated with peripheral nerve damage, central pain (i.e. due to cerebral ischemia) and various chronic pain i.e., lumbago, back pain (low back pain), inflammatory and/or rheumatic pain;

headache pain (for example, migraine with aura, migraine without aura, and other migraine disorders), episodic and chronic tension-type headache, tension-type like headache, cluster headache, and chronic paroxysmal hemicrania;

visceral pain such as pancreatits, intestinal cystitis, dysmenorrhea, irritable Bowel syndrome, Crohn's disease, biliary colic, ureteral colic, myocardial infarction and pain syndromes of the pelvic cavity, e.g., vulvodynia, orchialgia, urethral syndrome 15 and protatodynia;

acute pain, for example postoperative pain, and pain after trauma;

disorders associated with rheumatic disorders, e.g. including arthritis, rheumatoid arthritis, osteoarthritis, psoriatic arthritis, crystal arthropathies, gout, pseudogout, calcium pyrophosphate deposition disease, lupus syndromes, systemic lupus erythematosus, sclerosis, sclerodema, multiple sclerosis, artherosclerosis, arteriosclerosis, spondyloarthropathies, systemic sclerosis, reactive arthritis, Reiter's syndrome, ankylosing spondylitis, polymyositis, disorders associated with sarcoidosis, disorders associated with transplantation, e.g. including transplant rejection crisis and other disorders following transplantation, such as organ or tissue (xeno) transplant rejection, e.g. for the treatment of recipients of e.g. heart, lung, combined heart-lung, liver, kidney, pancreatic, skin, corneal transplants, graft versus host disease, such as following bone marrow transplantation, ischemic reperfusion injury, birth control (via inhibition of ovulation).

Although inhibition of ovulation is not a disorder, birth control (via inhibition of ovulation) is also meant to be encompassed by the definition of "Disorders which are prone to be mediated by CCR9 activity" according to the present invention.

Disorders which are prone to be mediated by CCR9 e.g. include preferably autoimmune disorders, inflammatory disorders, allergic disorders, disorders following transplantation, cancer;

more preferably autoimmune disorders, inflammatory disorders, disorders following transplantation;

such as

Coeliac disease, food allergy, rheumatoid arthritis, inflammatory bowel diseases (IBD), Crohn's disease, ulcerative colitis, psoriasis, atopic dermatitis, asthma, fibrotic diseases, diseases following transplantation, GVH rejection, cancer, leukemia (acute lymphocytic leukemia), solid tumors, carcinoids, thymoma, thymic carcinoma, preferably IBD, such as Crohn's disease, ulcerative colitis, e.g. including ulcerative proctitis.

In another aspect the present invention provides a compound of the present invention for use as a pharmaceutical, the use of a compound of the present invention as a pharmaceutical, the use of a compound of the present invention for the manufacture of a medicament, e.g. for the treatment of disorders mediated by CCR9 activity;

e.g. a compound of the present invention for the treatment of disorders mediated by CCR9 activity, such as disorders associated with the interruption of the binding of CCR9 to CCL25, such as disorders mediated by CCR9-mediated homing of leukocytes in a subject. for the treatment of disorders mediated by CCR9 activity.

In another aspect the present invention provides a compound of the present invention for the manufacture of a medicament for the treatment of inflammatory bowel disease For pharmaceutical use one or more compounds of the present invention may be used, e.g. a combination of two or more compounds of the present invention, preferably one compound of the present invention is used.

A compound of the present invention may be used as a pharmaceutical in the form of a pharmaceutical composition.

In another aspect the present invention provides a pharmaceutical composition comprising a compound of the present invention in association with at least one pharmaceutically acceptable excipient, e.g. appropriate carrier and/or diluent, e.g. including fillers, binders, disintegrants, flow conditioners, lubricants, sugars or sweeteners, fragrances, preservatives, stabilizers, wetting agents and/or emulsifiers, solubilizers, salts for regulating osmotic pressure and/or buffers.

In another aspect the present invention provides
a pharmaceutical composition of the present invention for use of treating disorders which are mediated by CCR9 activity.
the use of a pharmaceutical composition of the present invention for treating disorders which are mediated by CCR9 activity;
the use of a pharmaceutical composition comprising a compound of the present invention for the treatment of inflammatory bowel disease.
the use of a pharmaceutical composition comprising a compound of the present invention for treating disorders which are mediated by CCR9 activity.

Treatment of disorders (diseases) as used herein includes prophylaxis (prevention).

For such treatment, the appropriate dosage will, of course, vary depending upon, for example, the chemical nature and the pharmacokinetic data of a compound of the present invention used, the individual host, the mode of administration and the nature and severity of the conditions being treated. However, in general, for satisfactory results in larger mammals, for example humans, an indicated daily dosage includes a range
from about 0.0001 g to about 1.5 g, such as 0.001 g to 1.5 g,
from about 0.001 mg/kg body weight to about 20 mg/kg body weight, such as 0.01 mg/kg body weight to 20 mg/kg body weight, of a compound of the present invention, for example administered in divided doses up to four times a day.

A compound of the present invention may be administered to larger mammals, for example humans, by similar modes of administration than conventionally used with other mediators, e.g. low molecular weight inhibitors, of CCR9 activity.

In a further aspect the present invention provides a method of treating disorders which are mediated by CCR9 activity, e.g. including disorders as specified above, which treatment comprises administering to a subject in need of such treatment a therapeutically effective amount of a compound of the present invention; e.g. in the form of a pharmaceutical composition.

In another aspect the present invention provides
a compound of the present invention for the manufacture of a medicament,
the use of a compound of the present invention for the manufacture of a medicament,
e.g. a pharmaceutical composition,
for the treatment of disorders, which are mediated by CCR9 activity.

In a further aspect the present invention provides a method of treating inflammatory bowel disease, which treatment comprises administering to a subject in need of such treatment a therapeutically effective amount of a compound of the present invention; e.g. in the form of a pharmaceutical composition.

A compound of the present invention may be administered by any conventional route, for example enterally, e.g. including nasal, buccal, rectal, oral administration; parenterally, e.g. including intravenous, intraarterial, intramuscular, intracardiac, subcutaneous, intraosseous infusion, transdermal (diffusion through the intact skin), transmucosal (diffusion through a mucous membrane), inhalational administration; topically; e.g. including epicutaneous, intranasal, intratracheal administration; intraperitoneal (infusion or injection into the peritoneal cavity); epidural (peridural) (injection or infusion into the epidural space); intrathecal (injection or infusion into the cerebrospinal fluid); intravitreal (administration via the eye); or via medical devices, e.g. for local delivery, e.g. stents, e.g. in form of coated or uncoated tablets, capsules, (injectable) solutions, infusion solutions, solid solutions, suspensions, dispersions, solid dispersions; e.g. in the form of ampoules, vials, in the form of creams, gels, pastes, inhaler powder, foams, tinctures, lip sticks, drops, sprays, or in the form of suppositories.

For topical use, e.g. including administration to the eye, satisfactory results may be obtained with local administration of a 0.5-10%, such as 1-3% concentration of active substance several times daily, e.g. 2 to 5 times daily.

A compound of the present invention may be administered in the form of a pharmaceutically acceptable salt, e.g. an acid addition salt or metal salt; or in free form; optionally in the form of a solvate. A compound of the present invention in the form of a salt exhibit the same order of activity as a compound of the present invention in free form; optionally in the form of a solvate.

A compound of the present invention may be used for any method or use as described herein alone or in combination with one or more, at least one, other, second drug substance.

In another aspect the present invention provides
A combination of a compound of the present invention with at least one second drug substance;
A pharmaceutical combination comprising a compound of the present invention in combination with at least one second drug substance;
A pharmaceutical composition comprising a compound of the present invention in combination with at least one second drug substance and one or more pharmaceutically acceptable excipient(s);
A compound of the present invention in combination with at least one second drug substance, e.g. in the form of a pharmaceutical combination or composition, for use in any method as defined herein, e.g.
A combination, a pharmaceutical combination or a pharmaceutical composition, comprising a compound of the present invention and at least one second drug substance for use as a pharmaceutical;
The use as a pharmaceutical of a compound of the present invention in combination with at least one second drug substance, e.g. in the form of a pharmaceutical combination or composition;
The use of a compound of the present invention for the manufacture of a medicament for use in combination with a second drug substance; e.g. for any therapeutical treatment as indicated herein;
A method for treating disorders mediated by CCR9 activity in a subject in need thereof, comprising co-administering, concomitantly or in sequence, a therapeutically effective amount of a compound of the present invention and at least one second drug substance, e.g. in the form of a pharmaceutical combination or composition;
A compound of the present invention in combination with at least one second drug substance, e.g. in the form of a pharmaceutical combination or composition, for use in the preparation of a medicament for use in disorders mediated by CCR9 activity.

Combinations include fixed combinations, in which a compound of the present invention and at least one second drug substance are in the same formulation; kits, in which a compound of the present invention and at least one second drug substance in separate formulations are provided in the same package, e.g. with instruction for co-administration; and free combinations in which a compound of the present invention and at least one second drug substance are packaged separately, but instruction for concomitant or sequential administration are given.

In another aspect the present invention provides
A pharmaceutical package comprising a first drug substance which is a compound of the present invention and at least one second drug substance, beside instructions for combined administration;
A pharmaceutical package comprising a compound of the present invention beside instructions for combined administration with at least one second drug substance;
A pharmaceutical package comprising at least one second drug substance beside instructions for combined administration with a compound of the present invention.

Treatment with combinations according to the present invention may provide improvements compared with single treatment.

In another aspect the present invention provides
A pharmaceutical combination comprising an amount of a compound of the present invention and an amount of a second drug substance, wherein the amounts are appropriate to produce a synergistic therapeutic effect;
A method for improving the therapeutic utility of compound of the present invention comprising co-administering, e.g. concomitantly or in sequence, of a therapeutically effective amount of compound of the present invention and a second drug substance.
A method for improving the therapeutic utility of a second drug substance comprising co-administering, e.g. concomitantly or in sequence, of a therapeutically effective amount of compound of the present invention and a second drug substance.

A combination of the present invention and a second drug substance as a combination partner may be administered by any conventional route, for example as set out above for a compound of the present invention. A second drug may be administered in dosages as appropriate, e.g. in dosage ranges which are similar to those used for single treatment, or, e.g. in case of synergy, even below conventional dosage ranges.

Pharmaceutical compositions according to the present invention may be manufactured according, e.g. analogously, to a method as conventional, e.g. by mixing, granulating, coating, dissolving or lyophilizing processes. Unit dosage forms may contain, for example, from about 0.1 mg to about 1500 mg, such as 1 mg to about 1000 mg.

Pharmaceutical compositions comprising a combination of the present invention and pharmaceutical compositions comprising a second drug as described herein, may be provided as appropriate, e.g. according, e.g. analogously, to a method as conventional, or as described herein for a pharmaceutical composition of the present invention.

By the term "second drug substance" is meant a chemotherapeutic drug, especially any chemotherapeutic agent, other than an agent of the present invention.

For example, a second drug substance as used herein includes
other CCR9 inhibitors than a compound of the present invention e.g. including antibodies and low molecular weight compounds,
anti-inflammatory and/or immunomodulatory drugs,
antiallergic drugs
anticancer drugs
anesthetic drugs
antidiarrheal drugs.

For IBD-treatment the term "second drug substance" is meant to include an anti-inflammatory and/or an immunomodulatory drug, e.g. including a drug which is active in IBD prevention or treatment and/or which is active in treating manifestations of IBD, e.g. IBD symptoms, such as an anesthetic drug or an antidiarrheal drug.

Anti-inflammatory and/or immunomodulatory drugs which are prone to be useful in combination with a compound of the present invention include e.g.
mediators, e.g. inhibitors, of mTOR activity, including rapamycin of formula

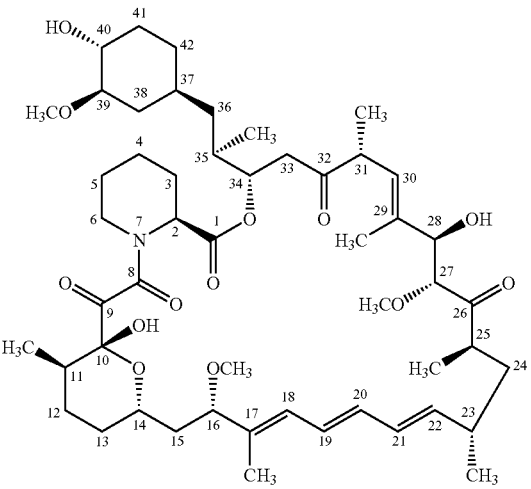

and rapamycin derivatives, e.g. including
40-O-alkyl-rapamycin derivatives, such as 40-O-hydroxyalkyl-rapamycin derivatives, such as 40-O-(2-hydroxy)-ethyl-rapamycin (everolimus),
32-deoxo-rapamycin derivatives and 32-hydroxy-rapamycin derivatives, such as 32-deoxorapamycin,
16-O-substituted rapamycin derivatives such as 16-pent-2-ynyloxy-32-deoxorapamycin, 16-pent-2-ynyloxy-32 (S or R)-dihydro-rapamycin, 16-pent-2-ynyloxy-32(S or R)-dihydro-40-O-(2-hydroxyethyl)-rapamycin,
rapamycin derivatives which are acylated at the oxygen group in position 40, e.g. 40-[3-hydroxy-2-(hydroxy-methyl)-2-methylpropanoate]-rapamycin (also known as CCI779), rapamycin derivatives which are substituted in 40 position by heterocyclyl, e.g. 40-epi-(tetrazolyl)-rapamycin (also known as ABT578),
the so-called rapalogs, e.g. as disclosed in WO9802441, WO0114387 and WO0364383, such as AP23573, and
compounds disclosed under the name TAFA-93, AP23464, AP23675, AP23841 and biolimus (e.g. biolimus A9).
mediators, e.g. inhibitors, of calcineurin, e.g. cyclosporin A, FK 506;
ascomycins having immuno-suppressive properties, e.g. ABT-281, ASM981;
corticosteroids; cyclophosphamide; azathioprene; leflunomide; mizoribine;
mycophenolic acid or salt; e.g. sodium, mycophenolate mofetil;
15-deoxyspergualine or an immunosuppressive homologue, analogue or derivative thereof;
mediators, e.g. inhibitors, of bcr-abl tyrosine kinase activity;
mediators, e.g. inhibitors, of c-kit receptor tyrosine kinase activity;
mediators, e.g. inhibitors, of PDGF receptor tyrosine kinase activity, e.g. Gleevec (imatinib);

mediators, e.g. inhibitors, of p38 MAP kinase activity, mediators, e.g. inhibitors, of VEGF receptor tyrosine kinase activity, mediators, e.g. inhibitors, of PKC activity, e.g. as disclosed in WO0238561 or WO0382859, e.g. the compound of Example 56 or 70;

mediators, e.g. inhibitors, of JAK3 kinase activity, e.g. N-benzyl-3,4-dihydroxy-benzylidene-cyanoacetamide α-cyano-(3,4-dihydroxy)-]N-benzylcinnamamide (Tyrphostin AG 490), prodigiosin 25-C (PNU156804), [4-(4'-hydroxyphenyl)-amino-6,7-dimethoxyquinazoline] (WHI-P131), [4-(3'-bromo-4'-hydroxylphenyl)-amino-6,7-dimethoxyquinazoline] (WHI-P154), [4-(3',5'-dibromo-4'-hydroxylphenyl)-amino-6,7-dimethoxyquinazoline] WHI-P97, KRX-211, 3-{(3R,4R)-4-methyl-3-[methyl-(7H-pyrrolo[2,3-d]pyrimidin-4-yl)-amino]-piperidin-1-yl}-3-oxo-propionitrile, in free form or in a pharmaceutically acceptable salt form, e.g. mono-citrate (also called CP-690,550), or a compound as disclosed in WO2004052359 or WO2005066156;

mediators, e.g. agonists or modulators of S1P receptor activity, e.g. FTY720 optionally phosphorylated or an analog thereof, e.g. 2-amino-2-[4-(3-benzyloxyphenylthio)-2-chlorophenyl]ethyl-1,3-propanediol optionally phosphorylated or 1-{4-[1-(4-cyclohexyl-3-trifluoromethyl-benzyloxyimino)-ethyl]-2-ethyl-benzyl}-azetidine-3-carboxylic acid or its pharmaceutically acceptable salts;

immunosuppressive monoclonal antibodies, e.g., monoclonal antibodies to leukocyte receptors, e.g., Blys/BAFF receptor, MHC, CD2, CD3, CD4, CD7, CD8, CD25, CD28, CD40, CD45, CD52, CD58, CD80, CD86, IL-12 receptor, IL-17 receptor, IL-23 receptor or their ligands;

other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4lg (for ex. designated ATCC 68629) or a mutant thereof, e.g. LEA29Y;

mediators, e.g. inhibitors of adhesion molecule activities, e.g. LFA-1 antagonists, ICAM-1 or -3 antagonists, VCAM-4 antagonists or VLA-4 antagonists, mediators, e.g. inhibitors, of MIF activity, 5-aminosalicylate (5-ASA) agents, such as sulfasalazine, Azulfidine®, Asacol®, Dipentum®, Pentasa®, Rowasa®, Canasa®, Colazal®, e.g. drugs containing mesalamine; e.g. mesalazine in combination with heparin;

mediators, e.g. inhibitors, of TNF-alpha activity, e.g. including antibodies which bind to TNF-alpha, e.g. infliximab (Remicade®), thalidomide, lenalidomide, nitric oxide releasing non-steriodal anti-inflammatory drugs (NSAIDs), e.g. including COX-inhibiting NO-donating drugs (CINOD);

phospordiesterase, e.g. mediators, such as inhibitors of PDE4B activity, mediators, e.g. inhibitors, of caspase activity, mediators, e.g. agonists, of the G protein coupled receptor GPBAR1, mediators, e.g. inhibitors, of ceramide kinase activity, 'multi-functional anti-inflammatory' drugs (MFAIDs), e.g. cytosolic phospholipase A2 (cPLA2) inhibitors, such as membrane-anchored phospholipase A2 inhibitors linked to glycosaminoglycans;

antibiotics, such as penicillins, cephalosporins, erythromycins, tetracyclines, sulfonamides, such as sulfadiazine, sulfisoxazole; sulfones, such as dapsone; pleuromutilins, fluoroquinolones, e.g. metronidazole, quinolones such as ciprofloxacin; levofloxacin; probiotics and commensal bacteria e.g. Lactobacillus, Lactobacillus reuteri;

antiviral drugs, such as ribivirin, vidarabine, acyclovir, ganciclovir, zanamivir, oseltamivir phosphate, famciclovir, atazanavir, amantadine, didanosine, efavirenz, foscarnet, indinavir, lamivudine, nelfinavir, ritonavir, saquinavir, stavudine, valacyclovir, valganciclovir, zidovudine.

Anti-inflammatory drugs which are prone to be useful in combination with a compound of the present invention include e.g. non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); cyclooxygenase-2 (COX-2) inhibitors such as celecoxib; inhibitors of phosphodiesterase type IV (PDE-IV); antagonists of the chemokine receptors, especially CCR1, CCR2, and CCR3; cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; anticholinergic agents such as muscarinic antagonists (ipratropium bromide); other compounds such as theophylline, sulfasalazine and aminosalicylates, e.g. 5-aminosalicylic acid and prodrugs thereof, antirheumatics.

Antiallergic drugs which are prone to be useful in combination with a compound of the present invention include e.g. antihistamines (H1-histamine antagonists), e.g. bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and non-steroidal anti-asthmatics such as β2-agonists (terbutaline, metaproterenol, fenoterol, isoetharine, albuterol, bitolterol, salmeterol and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); bronchodilators, antiasthmatics (mast cell stabilizers).

Anticancer drugs which are prone to be useful as a combination partner with a compound of the present invention, e.g. include i. a steroid; e.g. prednisone.

ii. an adenosine-kinase-inhibitor; which targets, decreases or inhibits nucleobase, nucleoside, nucleotide and nucleic acid metabolisms, such as 5-Iodotubercidin, which is also known as 7H-pyrrolo[2,3-d]pyrimidin-4-amine, 5-iodo-7-β-D-ribofuranosyl.

iii. an adjuvant; which enhances the 5-FU-TS bond as well as a compound which targets, decreases or inhibits, alkaline phosphatase, such as leucovorin, levamisole.

iv. an adrenal cortex antagonist; which targets, decreases or inhibits the activity of the adrenal cortex and changes the peripheral metabolism of corticosteroids, resulting in a decrease in 17-hydroxycorticosteroids, such as mitotane.

v. an AKT pathway inhibitor; such as a compound which targets, decreases or inhibits Akt, also known as protein kinase B (PKB), such as deguelin, which is also known as 3H-bis[1]benzopyrano[3,4-b:6',5'-e]pyran-7(7aH)-one, 13,13a-dihydro-9,10-dimethoxy-3,3-dimethyl-, (7aS, 13aS); and triciribine, which is also known as 1,4,5,6,8-pentaazaacenaphthylen-3-amine, 1,5-dihydro-5-methyl-1-β-D-ribofuranosyl.

vi. an alkylating agent; which causes alkylation of DNA and results in breaks in the DNA molecules as well as cross-linking of the twin strands, thus interfering with DNA replication and transcription of RNA, such as nitrogen mustards, e.g. chlorambucil, chlormethine, cyclophosphamide, ifosfamide, melphalan, estramustine (Emcyt®); nitrosueras, such as carmustine, fotemustine, lomustine, streptozocin (streptozotocin, STZ, Zanosar®), BCNU; Gliadel; dacarbazine, mechlorethamine, e.g. in the form of a hydrochloride, procarbazine, e.g. in the form of a hydrochloride, thiotepa, temozolomide (TEMODAR®), mitomycin, altretamine, busulfan, estramustine, uramustine. Cyclophosphamide can be administered, e.g., in the form as it is marketed, e.g., under the trademark CYCLOSTIN®; and ifosfamide as HOLOXAN®.

vii. an angiogenesis inhibitor; which targets, decreases or inhibits the production of new blood vessels, e.g. which targets methionine aminopeptidase-2 (MetAP-2), macrophage inflammatory protein-1 (MIP-1alpha), CCL5, TGF-beta, lipoxygenase, cyclooxygenase, and topoisomerase, or which indirectly targets p21, p53, CDK2 and collagen synthesis, e.g. including fumagillin, which is known as 2,4,6,8-decatetraenedioic acid, mono[(3R,4S,5S,6R)-5-methoxy-4-[(2R,3R)-2-methyl-3-(3-methyl-2-butenyl)oxiranyl]-1-oxaspiro[2.5]oct-6-yl] ester, (2E,4E,6E,8E)-(9Cl); shikonin, which is also known as 1,4-naphthalenedione, 5,8-dihydroxy-2-[(1R)-1-hydroxy-4-methyl-3-pentenyl]-(9Cl); tranilast, which is also known as benzoic acid, 2-[[3-(3,4-dimethoxyphenyl)-1-oxo-2-propenyl]amino]; ursolic acid; suramin; bengamide or a derivative thereof, thalidomide, TNP-470.

viii. an anti-androgen; which blocks the action of androgens of adrenal and testicular origin which stimulate the growth of normal and malignant prostatic tissue, such as nilutamide; bicalutamide (CASODEX®), which can be formulated, e.g., as disclosed in U.S. Pat. No. 4,636,505.

ix. an anti-estrogen; which antagonizes the effect of estrogens at the estrogen receptor level, e.g. including an aromatase inhibitor, which inhibits the estrogen production, i. e. the conversion of the substrates androstenedione and testosterone to estrone and estradiol, respectively, e.g. including atamestane, exemestane, formestane, aminoglutethimide, roglethimide, pyridoglutethimide, trilostane, testolactone, ketoconazole, vorozole, fadrozole, anastrozole, letrozole, toremifene; bicalutamide; flutamide; tamoxifen, tamoxifen citrate; tamoxifen; fulvestrant; raloxifene, raloxifene hydrochloride. Tamoxifen may be e.g. administered in the form as it is marketed, e.g., NOLVADEX®; and raloxifene hydrochloride is marketed as EVISTA®. Fulvestrant may be formulated as disclosed in U.S. Pat. No. 4,659,516 and is marketed as FASLODEX®.

x. an anti-hypercalcemia agent; which is used to treat hypercalcemia, such as gallium (III) nitrate hydrate; and pamidronate disodium.

xi. an antimetabolite; which inhibits or disrupts the synthesis of DNA resulting in cell death, such as folic acids, e.g. methotrexate, pemetrexed, raltitrexed; purins, e.g. 6-mercaptopurine, cladribine, clofarabine; fludarabine, thioguanine (tioguanine), 6-thioguanine, pentostatin (deoxycoformycin); cytarabine; flexuridine; fluorouracil; 5-fluorouracil (5-FU), floxuridine (5-FUdR), capecitabine; gemcitabine; gemcitabine hydrochloride; hydroxyurea (e.g. Hydrea®); DNA de-methylating agents, such as 5-azacytidine and decitabine; edatrexate; Capecitabine and gemcitabine can be administered e.g. in the marketed form, such as XELODA® and GEMZAR®.

xii. an apoptosis inducer; which induces the normal series of events in a cell that leads to its death, e.g. selectively inducing the X-linked mammalian inhibitor of apoptosis protein XIAP, or e.g. downregulating BCL-xL; such as ethanol, 2-[[3-(2,3-dichlorophenoxy)propyl]amino]; gambogic acid; embelin, which is also known as 2,5-cyclohexadiene-1,4-dione, 2,5-dihydroxy-3-undecyl-(9Cl); arsenic trioxide.

xiii. an aurora kinase inhibitor; which targets, decreases or inhibits later stages of the cell cycle from the G2/M check point all the way through to the mitotic checkpoint and late mitosis; such as binucleine 2, which is also known as methanimidamide, N'-[1-(3-chloro4-fluorophenyl)-4-cyano-1H-pyrazol-5-yl]-N,N-dimethyl-(9Cl).

xiv. a Bruton's Tyrosine Kinase (BTK) inhibitor; which targets, decreases or inhibits human and murine B cell development; such as terreic acid.

xv. a calcineurin inhibitor; which targets, decreases or inhibits the T cell activation pathway, such as cypermethrin, which is also known as cyclopropanecarboxylic acid, 3-(2,2-dichloroethenyl)-2,2-dimethyl-, cyano (3-phenoxyphenyl)methyl ester; deltamethrin, which is also known as cyclopropanecarboxylic aci, 3-(2,2-dibromoethenyl)-2,2-dimethyl-(S)-cyano(3-phenoxyphenyl)methyl ester, (1R,3R); fenvalerate, which is also known as benzeneacetic acid, 4-chloro-α-(1-methylethyl)-cyano(3-phenoxyphenyl)methyl ester; and Tyrphostin 8; but excluding cyclosporin or FK506.

xvi. a CaM kinase II inhibitor; which targets, decreases or inhibits CaM kinases; constituting a family of structurally related enzymes that include phosphorylase kinase, myosin light chain kinase, and CaM kinases I-IV; such as 5-isoquinolinesulfonic acid, 4-[(2S)-2-[(5-isoquinolinylsulfonyl)methylamino]-3-oxo-3-(4-phenyl-1-piperazinyl)propyl]phenyl ester (9Cl); benzenesulfonamide, N-[2-[[[3-(4-chlorophenyl)-2-propenyl]methyl]amino]methyl]phenyl]-N-(2-hydroxyethyl)-4-methoxy.

xvii. a CD45 tyrosine phosphatase inhibitor; which targets, decreases or inhibits dephosphorylating regulatory pTyr residues on Src-family protein-tyrosine kinases, which aids in the treatment of a variety of inflammatory and immune disorders; such as phosphonic acid, [[2-(4-bromophenoxy)-5-nitrophenyl]hydroxymethyl].

xviii. a CDC25 phosphatase inhibitor; which targets, decreases or inhibits overexpressed dephosphorylate cyclin-dependent kinases in tumors; such as 1,4-naphthalenedione, 2,3-bis[(2-hydroyethyl)thio].

xix. a CHK kinase inhibitor; which targets, decreases or inhibits overexpression of the antiapoptotic protein Bcl-2; such as debromohymenialdisine. Targets of a CHK kinase inhibitor are CHK1 and/or CHK2.

xx. a controlling agent for regulating genistein, olomucine and/or tyrphostins; such as daidzein, which is also known as 4H-1-benzopyran-4-one, 7-hydroxy-3-(4-hydroxyphenyl); Iso-Olomoucine, and Tyrphostin 1.

xxi. a cyclooxygenase inhibitor; e.g. including Cox-2 inhibitors; which targets, decreases or inhibits the enzyme Cox-2 (cyclooxygenase-2); such as 1H-indole-3-acetamide, 1-(4-chlorobenzoyl)-5-methoxy-2-methyl-N-(2-phenylethyl); 5-alkyl substituted 2-arylaminophenylacetic acid and derivatives, e.g. celecoxib (CELEBREX®), rofecoxib (VIOXX®), etoricoxib, valdecoxib; or a 5-alkyl-2-arylaminophenylacetic acid, e.g., 5-methyl-2-(2'-chloro-6'-fluoroanilino)phenyl acetic acid, lumiracoxib; and celecoxib.

xxii. a cRAF kinase inhibitor; which targets, decreases or inhibits the up-regulation of E-selectin and vascular adhesion molecule-1 induced by TNF; such as 3-(3,5-dibromo-4-hydroxybenzylidene)-5-iodo-1,3-dihydroindol-2-one; and benzamide, 3-(dimethylamino)-N-[3-[(4-hydroxybenzoyl)amino]-4-methylphenyl]. Raf kinases play an important role as extracellular signal-regulating kinases in cell differentiation, proliferation, and apoptosis. A target of a cRAF kinase inhibitor includes, but is not limited, to RAF1.

xxiii. a cyclin dependent kinase inhibitor; which targets, decreases or inhibits cyclin dependent kinase playing a role in the regulation of the mammalian cell cycle; such as N9-isopropyl-olomoucine; olomoucine; purvalanol B, which is also known as Benzoic acid, 2-chloro-4-[[2-[[(1R)-1-(hydroxymethyl)-2-methylpropyl]amino]-9-(1-methylethyl)-9H-purin-6-yl]amino]-(9Cl); roascovitine; indirubin, which is also known as 2H-indol-2-one, 3-(1,3-dihydro-3-oxo-2H-indol-2-ylidene)-1,3-dihydro-(9Cl); kenpaullone, which is also known as indolo[3,2-d][1]benzazepin-6(5H)-one, 9-bromo-7,12-dihydro-(9Cl); purvalanol A, which is also known as 1-Butanol, 2-[[6-[(3-chlorophenyl)amino]-9-(1-methylethyl)-9H-purin-2-yl]amino]-3-methyl-, (2R)-(9Cl); indirubin-3'-monooxime. Cell cycle progression is regulated by a series of sequential events that include the activation and subsequent inactivation of cyclin dependent kinases (Cdks) and cyclins. Cdks are a group of serine/threonine kinases that form active heterodimeric complexes by binding to their regulatory subunits, cyclins. Examples of targets of a cyclin dependent kinase inhibitor include, but are not limited to, CDK, AHR, CDK1, CDK2, CDK5, CDK4/6, GSK3beta, and ERK.

xxiv. a cysteine protease inhibitor; which targets, decreases or inhibits cystein protease which plays a vital role in mammalian cellular turnover and apotosis; such as 4-morpholinecarboxamide,N-[(1S)-3-fluoro-2-oxo-1-(2-phenylethyl)propyl]amino]-2-oxo-1-(phenylmethyl) ethyl].

xxv. a DNA intercalator; which binds to DNA and inhibits DNA, RNA, and protein synthesis; such as plicamycin, dactinomycin.

xxvi. a DNA strand breaker; which causes DNA strand scission and results in inhibition of DNA synthesis, ininhibition of RNA and protein synthesis; such as bleomycin.

xxvii. an E3 Ligase inhibitor; which targets, decreases or inhibits the E3 ligase which inhibits the transfer of ubiquitin chains to proteins, marking them for degradation in the proteasome; such as N-((3,3,3-trifluoro-2-trifluoromethyl)propionyl)sulfanilamide.

xxviii. an endocrine hormone; which by acting mainly on the pituitary gland causes the suppression of hormones in males, the net effect being a reduction of testosterone to castration levels; in females, both ovarian estrogen and androgen synthesis being inhibited; such as leuprolide; megestrol, megestrol acetate.

xxix. compounds targeting, decreasing or inhibiting the activity of the epidermal growth factor family of receptor tyrosine kinases (EGFR, ErbB2, ErbB3, ErbB4 as homo- or heterodimers), such as compounds, proteins or antibodies which inhibit members of the EGF receptor tyrosine kinase family, e.g. EGF receptor, ErbB1, ErbB2, ErbB3 and ErbB4 or bind to EGF or EGF-related ligands, and are in particular those compounds, proteins or monoclonal antibodies generically and specifically disclosed in WO 9702266, e.g. the compound of ex. 39, EP0564409, WO9903854, EP0520722, EP0566226, EP0787722, EP0837063, U.S. Pat. No. 5,747,498, WO9810767, WO9730034, WO9749688, WO9738983 and, especially, WO9630347, e.g. a compound known as CP 358774, WO9633980, e.g. a compound known as ZD 1839; and WO 9503283, e.g. a compound known as ZM105180, e.g. including the dual acting tyrosine kinase inhibitor (ErbB1 and ErbB2) lapatinib (GSK572016), e.g. lapatinib ditosylate; panituzumab, trastuzumab (HERCEPTIN®), cetuximab, iressa, OSI-774, CI-1033, EKB-569, GW-2016, E1.1, E2.4, E2.5, E6.2, E6.4, E2.11, E6.3 or E7.6.3, 7H-pyrrolo-[2,3-d] pyrimidine derivatives which are e.g. disclosed in WO03013541, erlotinib, gefitinib. Erlotinib can be administered in the form as it is marketed, e.g. TARCEVA®, and gefitinib as IRESSA®, human monoclonal antibodies against the epidermal growth factor receptor including ABX-EGFR.

xxx. an EGFR, PDGFR tyrosine kinase inhibitor; such as EGFR kinase inhibitors including tyrphostin 23, tyrphostin 25, tyrphostin 47, tyrphostin 51 and tyrphostin AG 825; 2-propenamide, 2-cyano-3-(3,4-dihydroxyphenyl)-N-phenyl-(2E); tyrphostin Ag 1478; lavendustin A; 3-pyridineacetonitrile, α-[(3,5-dichlorophenyl) methylene]-, (αZ); an example of an EGFR, PDGFR tyrosine kinase inhibitor e.g. includes tyrphostin 46. PDGFR tyrosine kinase inhibitor including tyrphostin 46. Targets of an EGFR kinase inhibitor include guanylyl cyclase (GC-C) HER2, EGFR, PTK and tubulin.

xxxi. a farnesyltransferase inhibitor; which targets, decreases or inhibits the Ras protein; such as a-hydroxyfarnesylphosphonic acid; butanoic acid, 2-[[(2S)-2-[[(2S,3S)-2-[[(2R)-2-amino-3-mercaptopropyl] amino]-3-methylpentyl]oxy]-1-oxo-3-phenylpropyl] amino]-4-(methylsulfonyl)-, 1-methylethyl ester, (2S); manumycin A; L-744,832 or DK8G557, tipifarnib (R115777), SCH66336 (lonafarnib), BMS-214662, xxxii. a Flk-1 kinase inhibitor; which targets, decreases or inhibits Flk-1 tyrosine kinase activity; such as 2-propenamide, 2-cyano-3-[4-hydroxy-3,5-bis(1-methylethyl) phenyl]-N-(3-phenylpropyl)-(2E). A target of a Flk-1 kinase inhibitor includes, but is not limited to, KDR.

xxxiii. a Glycogen synthase kinase-3 (GSK3) inhibitor; which targets, decreases or inhibits glycogen synthase kinase-3 (GSK3); such as indirubin-3'-monooxime. Glycogen Synthase Kinase-3 (GSK-3; tau protein kinase 1), a highly conserved, ubiquitously expressed serine/threonine protein kinase, is involved in the signal transduction cascades of multiple cellular processes. which is a protein kinase that has been shown to be involved in the regulation of a diverse array of cellular functions, including protein synthesis, cell proliferation, cell differentiation, microtubule assembly/disassembly, and apoptosis.

xxxiv. a histone deacetylase (HDAC) inhibitor; which inhibits the histone deacetylase and which possess antiproliferative activity; such as compounds disclosed in WO0222577, especially N-hydroxy-3-[4-[[(2-hydroxyethyl)[2-(1H-indol-3-yl)ethyl]-amino]methyl]phenyl]-2E-2-propenamide, and N-hydroxy-3-[4-[[[2-(2-methyl-1H-indol-3-yl)-ethyl]-amino]methyl]phenyl]-2E-2-propenamide and pharmaceutically acceptable salts thereof; suberoylanilide hydroxamic acid (SAHA); [4-(2-amino-phenylcarbamoyl)-benzyl]-carbamic acid pyridine-3-ylmethyl ester and derivatives thereof; butyric acid, pyroxamide, trichostatin A, oxamflatin, apicidin, depsipeptide; depudecin; trapoxin, HC toxin, which is also known as cyclo[L-alanyl-D-alanyl-(□S, 2S)-□-amino-□-oxooxiraneoctanoyl-D-prolyl] (9Cl); sodium phenylbutyrate, suberoyl bis-hydroxamic acid; Trichostatin A, BMS-27275, pyroxamide, FR-901228, valproic acid.

xxxv. a HSP90 inhibitor; which targets, decreases or inhibits the intrinsic ATPase activity of HSP90; degrades, targets, decreases or inhibits the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, e.g., 17-allylamino, 17-demethoxygeldanamycin (17AAG), a geldanamycin derivative; other geldanamycin-related compounds; radicicol and HDAC inhibitors. Other examples of an HSP90 inhibitor include geldanamycin,17-demethoxy-17-(2-propenylamino). Potential indirect targets of an HSP90 inhibitor include FLT3, BCR-ABL, CHK1, CYP3A5*3 and/or NQ01*2. Nilotinib is an example of an BCR-ABL tyrosine kinase inhibitor.

xxxvi. a I-kappa B-alpha kinase inhibitor (IKK); which targets, decreases or inhibits NF-kappaB, such as 2-propenenitrile, 3-[(4-methylphenyl)sulfonyl]-(2E).

xxxvii. an insulin receptor tyrosine kinase inhibitor; which modulates the activities of phosphatidylinositol 3-kinase, microtubule-associated protein, and S6 kinases; such as hydroxyl-2-naphthalenylmethylphosphonic acid, LY294002.

xxxviii. a c-Jun N-terminal kinase (JNK) kinase inhibitor; which targets, decreases or inhibits Jun N-terminal kinase; such as pyrazoleanthrone and/or epigallocatechin gallate. Jun N-terminal kinase (JNK), a serine-directed protein kinase, is involved in the phosphorylation and activation of c-Jun and ATF2 and plays a significant role in metabolism, growth, cell differentiation, and apoptosis. A target for a JNK kinase inhibitor includes, but is not limited to, DNMT.

xxxix a microtubule binding agent; which acts by disrupting the microtubular network that is essential for mitotic and interphase cellular function; such as vinca alkaloids, e.g. vinblastine, vinblastine sulfate; vincristine, vincristine sulfate; vindesine; vinorelbine; taxanes, such as taxanes, e.g. docetaxel; paclitaxel; discodermolides; cochicine, epothilones and derivatives thereof, e.g. epothilone B or a derivative thereof. Paclitaxel is marketed as TAXOL®; docetaxel as TAXOTERE®; vinblastine sulfate as VINBLASTIN R.P®; and vincristine sulfate as FARMISTIN®. Also included are the generic forms of paclitaxel as well as various dosage forms of paclitaxel. Generic forms of paclitaxel include, but are not limited to, betaxolol hydrochloride. Various dosage forms of paclitaxel include, but are not limited to albumin nanoparticle paclitaxel marketed as ABRAXANE®; ONXOL®, CYTOTAX®. Discodermolide can be obtained, e.g., as disclosed in U.S. Pat. No. 5,010,099. Also included are Epotholine derivatives which are disclosed in U.S. Pat. No. 6,194,181, WO98/0121, WO9825929, WO9808849, WO9943653, WO9822461 and WO0031247. Especially preferred are Epotholine A and/or B.

xl. a mitogen-activated protein (MAP) kinase-inhibitor; which targets, decreases or inhibits Mitogen-activated protein, such as benzenesulfonamide, N-[2-[[[3-(4-chlorophenyl)-2-propenyl]methyl]amino]methyl]phenyl]-N-(2-hydroxyethyl)4-methoxy. The mitogen-activated protein (MAP) kinases are a group of protein serine/threonine kinases that are activated in response to a variety of extracellular stimuli and mediate signal transduction from the cell surface to the nucleus. They regulate several physiological and pathological cellular phenomena, including inflammation, apoptotic cell death, oncogenic transformation, tumor cell invasion, and metastasis.

xli. a MDM2 inhibitor; which targets, decreases or inhibits the interaction of MDM2 and the p53 tumor suppressor; such as trans-4-iodo, 4'-boranyl-chalcone.

xlii. a MEK inhibitor; which targets, decreases or inhibits the kinase activity of MAP kinase MEK; such as sorafenib, e.g. Nexavar® (sorafenib tosylate), butanedinitrile, bis[amino[2-aminophenyl)thio]methylene]. A target of a MEK inhibitor includes, but is not limited to ERK. An indirect target of a MEK inhibitor includes, but is not limited to, cyclin D1.

xliii: a matrix metalloproteinase inhibitor (MMP) inhibitor; which targets, decreases or inhibits a class of protease enzyme that selectively catalyze the hydrolysis of polypeptide bonds including the enzymes MMP-2 and MMP-9 that are involved in promoting the loss of tissue structure around tumors and facilitating tumor growth, angiogenesis, and metastasissuch as actinonin, which is also known as butanediamide, N-4-hydroxy-N 1-[(1S)-1-[[(2S)-2-(hydroxymethyl)-1-pyrrolidinyl]carbonyl]-2-methylpropyl]-2-pentyl-, (2R)-(9Cl); epigallocatechin gallate; collagen peptidomimetic and non-peptidomimetic inhibitors; tetracycline derivatives, e.g., hydroxamate peptidomimetic inhibitor batimastat; and its orally-bioavailable analogue marimastat, prinomastat, metastat, neovastat, tanomastat, TAA211, BMS-279251, BAY 12-9566, MMI270B or MJ996. A target of a MMP inhibitor includes, but is not limited to, polypeptide deformylase.

xliv. a NGFR tyrosine-kinase-inhibitor; which targets, decreases or inhibits nerve growth factor dependent p140$^{c\text{-}trk}$ tyrosine phosphorylation; such as tyrphostin AG 879. Targets of a NGFR tyrosine-kinase-inhibitor include, but are not limited to, HER2, FLK1, FAK, TrkA, and/or TrkC. An indirect target inhibits expression of RAF1.

xlv. a p38 MAP kinase inhibitor, including a SAPK2/p38 kinase inhibitor; which targets, decreases or inhibits p38-MAPK, which is a MAPK family member, such as phenol, 4-[4-(4-fluorophenyl)-5-(4-pyridinyl)-1H-imidazol-2-yl]. An example of a a SAPK2/p38 kinase inhibitor includes, but is not limited to, benzamide, 3-(dimethylamino)-N-[3-[(4-hydroxybenzoyl)amino]-4-methylphenyl]. A MAPK family member is a serine/threonine kinase activated by phosphorylation of tyrosine and threonine residues. This kinase is phosphorylated and activated by many cellular stresses and inflammatory stimuli, thought to be involved in the regulation of important cellular responses such as apoptosis and inflammatory reactions.

xlvi. a p56 tyrosine kinase inhibitor; which targets, decreases or inhibits p56 tyrosine kinase, which is an enzyme that is a lymphoid-specific src family tyrosine kinase critical for T-cell development and activation; such as damnacanthal, which is also known as 2-anthracenecarboxaldehyde,9,10-dihydro-3-hydroxy-1 methoxy-9,10-dioxo, Tyrphostin 46. A target of a p56 tyrosine kinase inhibitor includes, but is not limited to, Lck. Lck is associated with the cytoplasmic domains of CD4, CD8 and the beta-chain of the IL-2 receptor, and is thought to be involved in the earliest steps of TCR-mediated T-cell activation.

xlvii. a PDGFR tyrosine kinase inhibitor; targeting, decreasing or inhibiting the activity of the C-kit receptor tyrosine kinases (part of the PDGFR family), such as targeting, decreasing or inhibiting the activity of the c-Kit receptor tyrosine kinase family, especially inhibiting the c-Kit receptor. Examples of targets of a PDGFR tyrosine kinase inhibitor includes, but are not limited to PDGFR, FLT3 and/or c-KIT; such as tyrphostin AG 1296; tyrphostin 9; 1,3-butadiene-1,1,3-tricarbonitrile, 2-amino-4-(1H-indol-5-yl); N-phenyl-2-pyrimidineamine derivative, e.g. imatinib, IRESSA®. PDGF plays a central role in regulating cell proliferation, chemotaxis, and survival in normal cells as well as in various disease states such as cancer, atherosclerosis, and fibrotic disease. The PDGF family is composed of dimeric isoforms (PDGF-M, PDGF-BB, PDGF-AB, PDGF-CC, and PDGF-DD), which exert their cellular effects by differentially binding to two receptor tyrosine kinases. PDGFR-α and PDGFR-β have molecular masses of ~170 and 180 kDa, respectively.

xlviii. a phosphatidylinositol 3-kinase inhibitor; which targets, decreases or inhibits PI 3-kinase; such as wortmannin, which is also known as 3H-Furo[4,3,2-de]indeno[4,5-h]-2-benzopyran-3,6,9-trione, 11-(acetyloxy)-1,6b,7,8,9a, 10,11,11 b-octahydro-1-(methoxymethyl)-9a,11b-dimethyl-, (1S,6bR,9aS,11R,11bR)-(9Cl); 8-phenyl-2-(morpholin-4-yl)-chromen-4-one; quercetin, quercetin dihydrate. PI 3-kinase activity has been shown to increase in response to a number of hormonal and growth factor stimuli, including insulin, platelet-derived growth factor, insulin-like growth factor, epidermal growth factor, colony-stimulating factor, and hepatocyte growth factor, and has been implicated in processes related to cellular growth and transformation. An example of a target of a phosphatidylinositol 3-kinase inhibitor includes, but is not limited to, Pi3K.

xlix. a phosphatase inhibitor; which targets, decreases or inhibits phosphatase; such as cantharidic acid; cantharidin; and L-leucinamide, N-[4-(2-carboxyethenyl)benzoyl]glycyl-L-α-glutamyl-(E). Phosphatases remove the phosphoryl group and restore the protein to its original dephosphorylated state. Hence, the phosphorylation-dephosphorylation cycle can be regarded as a molecular "on-off" switch.

l. platinum agent; which contains platinum and inhibit DNA synthesis by forming interstrand and intrastrand cross-linking of DNA molecules; such as carboplatin; cisplatin; oxaliplatin; cisplatinum; satraplatin and platinum agents such as ZD0473, BBR3464. Carboplatin can be administered, e.g., in the form as it is marketed, e.g. CARBOPLAT®; and oxaliplatin as ELOXATIN®.

li. a protein phosphatase inhibitor, including a PP1 and PP2 inhibitor and a tyrosine phosphatase inhibitor; which targets, decreases or inhibits protein phosphatase. Examples of a PP1 and PP2A inhibitor include cantharidic acid and/or cantharidin. Examples of a tyrosine phosphatase inhibitor include, but are not limited to, L-P-bromotetramisole oxalate; 2(5H)-furanone, 4-hydroxy-5-(hydroxymethyl)-3-(1-oxohexadecyl)-, (5R); and benzylphosphonic acid.

The term "a PP1 or PP2 inhibitor", as used herein, relates to a compound which targets, decreases or inhibits Ser/Thr protein phosphatases. Type I phosphatases, which include PP1, can be inhibited by two heat-stable proteins known as Inhibitor-1 (I-1) and Inhibitor-2 (I-2). They preferentially dephosphorylate a subunit of phosphorylase kinase. Type II phosphatases are subdivided into spontaneously active (PP2A), $CA^{2+}$-dependent (PP2B), and $Mg^{2+}$-dependent (PP2C) classes of phosphatases.

The term "tyrosine phosphatase inhibitor", as used here, relates to a compounds which targets, decreases or inhibits tyrosine phosphatase. Protein tyrosine phosphatases (PTPs) are relatively recent additions to the phosphatase family. They remove phosphate groups from phosphorylated tyrosine residues of proteins. PTPs display diverse structural features and play important roles in the regulation of cell proliferation, differentiation, cell adhesion and motility, and cytoskeletal function. Examples of targets of a tyrosine phosphatase inhibitor include, but are not limited to, alkaline phosphatase (ALP), heparanase, PTPase, and/or prostatic acid phosphatase.

lii. a PKC inhibitor and a PKC delta kinase inhibitor: The term "a PKC inhibitor", as used herein, relates to a compound which targets, decreases or inhibits protein kinase C as well as its isozymes. Protein kinase C (PKC), a ubiquitous, phospholipid-dependent enzyme, is involved in signal transduction associated with cell proliferation, differentiation, and apoptosis. Examples of a target of a PKC inhibitor include, but are not limited to, MAPK and/or NF-kappaB. Examples of a PKC inhibitor include, but are not limited to, 1-H-pyrrolo-2,5-dione,3-[1-[3-(dimethylamino)propyl]-1H-indol-3-yl]-4-(1H-indol-3-yl); bisindolylmaleimide IX; sphingosine, which is known as 4-octadecene-1,3-diol, 2-amino-, (2S,3R,4E)-(9Cl); staurosporine, which is known as 9,13-Epoxy-1H,9H-diindolo[1,2,3-gh:3',2',1'-lm]pyrrolo[3,4-j][1,7]benzodiazonin-1-one, staurosporine derivatives such as disclosed in EP0296110, e.g. midostaurin; 2,3,10,11,12,13-hexahydro-10-methoxy-9-methyl-11-(methylamino)-, (9S,10R,11R,13R)-(9Cl); tyrphostin 51; and hypericin, which is also known as phenanthro[1,10,9,8-opqra]perylene-7,14-dione, 1,3,4,6,8,13-hexahydroxy-10,11-dimethyl-, stereoisomer (6Cl,7Cl,8Cl,9Cl), UCN-01,safingol, BAY 43-9006, bryostatin 1, perifosine; llmofosine; RO 318220 and RO 320432; GO 6976; Isis 3521; LY333531/LY379196. The term "a PKC delta kinase inhibitor", as used herein, relates to a compound which targets, decreases or inhibits the delta isozymes of PKC. The delta isozyme is a conventional PKC isozymes and is $Ca^{2+}$-dependent. An example of a PKC delta kinase inhibitor includes, but is not limited to, Rottlerin, which is also known as 2-Propen-1-one, 1-[6-[(3-acetyl-2,4,6-trihydroxy-5-methylphenyl)methyl]-5,7-dihydroxy-2,2-dimethyl-2H-1-benzopyran-8-yl]-3-phenyl-, (2E)-(9Cl).

liii. a polyamine synthesis inhibitor; which targets, decreases or inhibits polyamines spermidine; such as DMFO, which is also known as (−)-2-difluoromethylornithin; N1, N12-diethylspermine 4HCl. The polyamines spermidine and spermine are of vital importance for cell proliferation, although their precise mechanism of action is unclear.

Tumor cells have an altered polyamine homeostasis reflected by increased activity of biosynthetic enzymes and elevated polyamine pools.

liv. a proteosome inhibitor; which targets, decreases or inhibits proteasome, such as aclacinomycin A; gliotoxin; PS-341; MLN 341; bortezomib; velcade. Examples of targets of a proteosome inhibitor include, but are not limited to, O(2)(−)-generating NADPH oxidase, NF-kappaB, and/or farnesyltransferase, geranyltransferase I.

lv. a PTP1 B inhibitor; which targets, decreases or inhibits PTP1B, a protein tyrosine kinase inhibitor; such as L-leucinamide, N-[4-(2-carboxyethenyl)benzoyl]glycyl-L-α-glutamyl-,(E).

lvi. a protein tyrosine kinase inhibitor including a SRC family tyrosine kinase inhibitor; a Syk tyrosine kinase inhibitor; and a JAK-2 and/or JAK-3 tyrosine kinase inhibitor;

The term "a protein tyrosine kinase inhibitor", as used herein, relates to a compound which which targets, decreases or inhibits protein tyrosine kinases. Protein tyrosine kinases (PTKs) play a key role in the regulation of cell proliferation, differentiation, metabolism, migration, and survival. They are classified as receptor PTKs and non-receptor PTKs. Receptor PTKs contain a single polypeptide chain with a transmembrane segment. The extracellular end of this segment contains a high affinity ligand-binding domain, while the cytoplasmic end comprises the catalytic core and the regulatory sequences. Examples of targets of a tyrosine kinase inhibitor include, but are not limited to, ERK1, ERK2, Bruton's tyrosine kinase (Btk), JAK2, ERK ½, PDGFR, and/or FLT3. Examples of indirect targets include, but are not limited to, TNFalpha, NO, PGE2, IRAK, iNOS, ICAM-1, and/or E-selectin. Examples of a tyrosine kinase inhibitor include, but are not limited to, tyrphostin AG 126; tyrphostin Ag 1288; tyrphostin Ag 1295; geldanamycin; and genistein.

Non-receptor tyrosine kinases include members of the Src, Tec, JAK, Fes, Abl, FAK, Csk, and Syk families. They are located in the cytoplasm as well as in the nucleus. They exhibit distinct kinase regulation, substrate phosphorylation, and function. Deregulation of these kinases has also been linked to several human diseases. The term "a SRC family tyrosine kinase inhibitor", as used herein, relates to a compound which which targets, decreases or inhibits SRC. Examples of a SRC family tyrosine kinase inhibitor include, but are not limited to, PP1, which is also known as 1H-pyrazolo[3,4-d]pyrimidin-4-amine, 1-(1,1-dimethylethyl)-3-(1-naphthalenyl)-(9Cl); and PP2, which is also known as 1H-Pyrazolo[3,4-d]pyrimidin-4-amine, 3-(4-chlorophenyl)-1-(1,1-dimethylethyl)-(9Cl).

The term "a Syk tyrosine kinase inhibitor", as used herein, relates to a compound which targets, decreases or inhibits Syk. Examples of targets for a Syk tyrosine kinase inhibitor include, but are not limited to, Syk, STAT3, and/or STAT5. An example of a Syk tyrosine kinase inhibitor includes, but is not limited to, piceatannol, which is also known as 1,2-benzenediol, 4-[(1E)-2-(3,5-dihydroxyphenyl)ethenyl]-(9Cl).

The term "a Janus (JAK-2 and/or JAK-3) tyrosine kinase inhibitor", as used herein, relates to a compound which targets, decreases or inhibits janus tyrosine kinase. Janus tyrosine kinase inhibitor are shown anti-leukemic agents with anti-thrombotic, anti-allergic and immunosuppressive properties. Targets of a JAK-2 and/or JAK-3 tyrosine kinase inhibitor include, but are not limited to, JAK2, JAK3, STAT3. An indirect target of an JAK-2 and/or JAK-3 tyrosine kinase inhibitor includes, but is not limited to CDK2. Examples of a JAK-2 and/or JAK-3 tyrosine kinase inhibitor include, but are not limited to, Tyrphostin AG 490; and 2-naphthyl vinyl ketone. Compounds which target, decrease or inhibit the activity of c-Abl family members and their gene fusion products, e.g. include PD180970; AG957; or NSC 680410.

lvii. a retinoid; which target, decrease or inhibit retinoid dependent receptors; such as isotretinoin, tretinoin, alitretinoin, bexarotene.

lviii. a RNA polymerase 11 elongation inhibitor; which targets, decreases or inhibits insulin-stimulated nuclear and cytosolic p70S6 kinase in CHO cells; targets, decreases or inhibits RNA polymerase II transcription, which may be dependent on casein kinase II; and targets, decreases or inhibits germinal vesicle breakdown in bovine oocytes; such as 5,6-dichloro-1-beta-D-ribofuranosylbenzimidazole.

lvix. a serine/threonine kinase inhibitor; which inhibits serine/threonine kinases; such as 2-aminopurine. An example of a target of a serine/threonine kinase inhibitor includes, but is not limited to, dsRNA-dependent protein kinase (PKR). Examples of indirect targets of a serine/threonine kinase inhibitor include, but are not limited to, MCP-1, NF-kappaB, elF2alpha, COX2, RANTES, IL8, CYP2A5, IGF-1, CYP2B1, CYP2B2, CYP2H1, ALAS-1, HIF-1, erythropoietin, and/or CYP1A1.

lx. a sterol biosynthesis inhibitor; which inhibits the biosynthesis of sterols such as cholesterol; such as terbinadine. Examples of targets for a sterol biosynthesis inhibitor include, but are not limited to, squalene epoxidase, and CYP2D6.

lxi. a topoisomerase inhibitor; including a topoisomerase I inhibitor and a topoisomerase II inhibitor. Examples of a topoisomerase I inhibitor include, but are not limited to, topotecan, gimatecan, irinotecan, camptothecan and its analogues, 9-nitrocamptothecin and the macromolecular camptothecin conjugate PNU-166148 (compound A1 in WO9917804); 10-hydroxycamptothecin e.g. the acetate salt;

idarubicin, e.g. the hydrochloride; irinotecan, e.g. the hydrochloride; etoposide;

teniposide; topotecan, topotecan hydrochloride; doxorubicin; epirubicin, epirubicin hydrochloride; mitoxantrone, mitoxantrone, e.g. the hydrochloride; daunorubicin, daunorubicin hydrochloride, valrubicin, dasatinib (BMS-354825). Irinotecan can be administered, e.g., in the form as it is marketed, e.g., under the trademark CAMPTOSAR®. Topotecan can be administered, e.g., in the form as it is marketed, e.g., under the trademark HYCAMTIN®. The term "topoisomerase II inhibitor", as used herein, includes, but is not limited to, the anthracyclines, such as doxorubicin, including liposomal formulation, e.g., CAELYX®, daunorubicin, including liposomal formulation, e.g., DAUNOSOME®, epirubicin, idarubicin and nemorubicin; the anthraquinones mitoxantrone and losoxantrone; and the podophillotoxines etoposide and teniposide. Etoposide is marketed as ETOPOPHOS®; teniposide as VM 26-BRISTOL®; doxorubicin as ADRIBLASTIN® or ADRIAMYCIN®; epirubicin as FARMORUBICIN® idarubicin as ZAVEDOS®; and mitoxantrone as NOVANTRON®.

lxii. VEGFR tyrosine kinase inhibitor; which targets, decreases and/or inhibits the known angiogenic growth factors and cytokines implicated in the modulation of normal and pathological angiogenesis. The VEGF family (VEGF-A, VEGF-B, VEGF-C, VEGF-D) and their corresponding receptor tyrosine kinases [VEGFR-1 (Flt-1), VEGFR-2 (Flk-1, KDR), and VEGFR-3 (Flt-4)] play a paramount and indispensable role in regulating the multiple facets of the angiogenic and lymphangiogenic processes. An example of a VEGFR tyrosine kinase inhibitor includes 3-(4-dimethylaminobenzylidenyl)-2-indolinone. Compounds which target, decrease or inhibit the activity of VEGFR are especially compounds, proteins or antibodies which inhibit the VEGF receptor tyrosine kinase, inhibit a VEGF receptor or bind to VEGF, and are in particular those compounds, proteins or monoclonal antibodies generically and specifically disclosed in WO9835958, e.g. 1-(4-chloroanilino)-4-(4-pyridylmethyl) phthalazine or a pharmaceutical acceptable salt thereof, e.g. the succinate, or in WO0009495, WO0027820, WO0059509, WO9811223, WO0027819 and EP0769947; e.g. those as described by M. Prewett et al in Cancer Research 59 (1999) 5209-5218, by F. Yuan et al in Proc. Natl. Acad. Sci. USA, vol. 93, pp. 14765-14770, December 1996, by Z. Zhu et al in Cancer Res. 58,1998,3209-3214, and by J. Mordenti et al in Toxicologic Pathology, Vol. 27, no. 1, pp 14-21, 1999; in WO0037502 and WO9410202; Angiostatin, described by M. S. O'Reilly et al, Cell 79,1994,315-328; Endostatin described by M. S. O'Reilly et al, Cell 88,1997,277-285; anthranilic acid amides; ZD4190; ZD6474 (vandetanib); SU5416; SU6668; or anti-VEGF antibodies or anti-VEGF receptor antibodies, e.g. RhuMab (bevacizumab). By antibody is meant intact monoclonal antibodies, polyclonal antibodies, multispecific antibodies formed from at least 2 intact antibodies, and antibodies fragments so long as they exhibit the desired biological activity. an example of an VEGF-R2 inhibitor e.g. includes axitinib, lxiii. a gonadorelin agonist, such as abarelix, goserelin, goserelin acetate, lxiv. a compound which induce cell differentiation processes, such as retinoic acid, alpha-, gamma- or 8-tocopherol or alpha-, gamma- or 8-tocotrienol.

lxv. a bisphosphonate, e.g. including etridonic, clodronic, tiludronic, pamidronic, alendronic, ibandronic, risedronic and zoledronic acid.

lxvi. a heparanase inhibitor which prevents heparan sulphate degradation, e.g. PI-88, lxvii. a biological response modifier, preferably a lymphokine or interferons, e.g. interferon alpha, lxviii. a telomerase inhibitor, e.g. telomestatin, lxix. mediators, such as inhibitors of catechol-O-methyl-transferase, e.g. entacapone, lxx: ispinesib, permetrexed (Alimta®), sunitinib (SU11248), diethylstilbestrol (DES), BMS224818 (LEA29Y), lxxi somatostatin or a somatostatin analogue, such as octreotide (Sandostatin® or Sandostatin LAR®).

lxxii. Growth Hormone—Receptor Antagonists, such as pegvisomant, filgrastim or pegfilgrastim, or interferon alpha:

lxxiii. monoclonal antibodies, e.g. useful for leukemia (AML) treatment, such as alemtuzumab (Campath®), rituximab/Rituxan®), gemtuzumab, (ozogamicin, Mylotarg®), epratuzumab.

lxxiv. altretamine, amsacrine, asparaginase (Elspar®), denileukin diftitox, masoprocol, pegaspargase.

lxxv. a phosphodiesterase inhibitor, e.g. anagrelide (Agrylin®, Xagrid®).

lxxvi. a cancer vaccine, such as MDX-1379.

Cancer treatment with a compound of the present invention, optionally in combination with an anticancer drug, such as indicated herein, may be associated with radiotherapy. Cancer treatment with a compound of the present invention, optionally in combination with an anticancer drug, may be a second line treatment, e.g. following treatment with another anticancer drug or other cancer therapy.

Anesthetics which are prone to be useful as a combination partner with a compound of the present invention e.g. include ethanol, bupivacaine, chloroprocaine, levobupivacaine, lidocaine, mepivacaine, procaine, ropivacaine, tetracaine, desflurane, isoflurane, ketamine, propofol, sevoflurane, codeine, fentanyl, hydromorphone, marcaine, meperidine, methadone, morphine, oxycodone, remifentanil, sufentanil, butorphanol, nalbuphine, tramadol, benzocaine, dibucaine, ethyl chloride, xylocaine, and phenazopyridine.

Antidiarrheal drug substances which are prone to be useful as a combination partner with an agent or an IBD-agent of the present invention, e.g. include diphenoxylate, loperamide, codeine.

If a compound of the present invention is administered in combination with other drug substances dosages of the co-administered second drug substance will of course vary depending on the type of co-drug employed, on the specific drug employed, on the condition being treated, as in case of a compound of the present invention. In general dosages similar than those as provided by the second drug supplier may be appropriate The chemical names of the compounds of the present invention as indicated herein are copied from ISIS, version 2.5 (AutoNom 2000 Name). Chemical names of second drug substances and other substances may be derived from the Internet, e.g. via a search program such as the SCI FINDER.

In the following Examples all temperatures are in ° Celsius. The following ABBREVIATIONS are used:

| EtAc | ethyl acetate |
|---|---|
| RT | room temperature |

EXAMPLE 1

4-tert.Butyl-N-(4-chloro-2-cyano-phenyl)-benzenesulfonamide

A solution of 0.15 g of 2-amino-5-chloro-benzonitrile and 0.23 g of 4-tert.butyl-benzenesulfonyl chloride is dissolved in 2 ml of NMP (N-methyl 2-pyyrolidone) and cooled in an ice bath to 5°. 2.5 ml of a solution of potassium-tert.butylat (1 N in THF) is added, the mixture obtained is stirred for 30 min, quenched with water and from the mixture obtained solvent is evaporated. The evaporation residue is dissolved in EtAc, washed with saturated NaHCO₃ solution and dried. Solvent is evaporated and the evaporation residue is subjected to chromatography on a reversed phase column. 4-tert.Butyl-N-(4-chloro-2-cyano-phenyl)-benzenesulfonamide is obtained.

¹H-NMR (DMSO): 1.27 (s, 9H), 7.06 (d, J=8.5 Hz, 1H), 7.57-7.70 (m, 5H), 7.99 (d, J=2 Hz, 1H), 10.6 (broad s, 1H, NH).

Analogously to the methods as described in Examples 1 to 3, but using appropriate starting materials (intermediates) compounds of formula

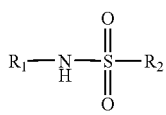

I wherein $R_1$ and $R_2$ are as set out in TABLE 1 below, having a melting point m.p. (° C.) as defined in TABLE 1 below, are obtained:

TABLE 1

| CP | R₁ | R₂ | Data |
|---|---|---|---|
| 1 | 4-cyano-2-methyl-phenyl (NC-phenyl with CH₃) | 5-chloro-thien-2-yl | 116-119 |
| 2 | 4-chloro-2-cyano-phenyl | 4,5-dichloro-thien-2-yl | 135-138 |
| 3 | 4-cyano-2-trifluoromethoxy-phenyl | 4,5-dichloro-thien-2-yl | 155-158 |
| 4 | 4-cyano-2-chloro-phenyl | 4,5-dichloro-thien-2-yl | 168-171 |
| 5 | 4-chloro-2-methyl-phenyl (with CN) | 5-chloro-thien-2-yl | 108-110 |

TABLE 1-continued

| CP | R₁ | R₂ | Data |
|---|---|---|---|
| 6 | 4-cyano-2-trifluoromethoxy-phenyl | 3-bromo-2,5-dichloro-4-methyl-thienyl | 183-185 |
| 7 | 4-chloro-2-methyl-phenyl (CN) | 3-bromo-2,5-dichloro-thienyl | 124-126 |
| 8 | 4-cyano-2-trifluoromethoxy-phenyl | 5-chloro-methyl-thien-2-yl | 155-157 |
| 9 | 4-cyano-2-trifluoromethoxy-phenyl | 2,5-dichloro-methyl-thienyl | 153-156 |
| 10 | 4-chloro-2-methyl-phenyl (CN) | 2,5-dichloro-methyl-thienyl | 140-143 |

"CP" in TABLE 1 means "Compound number"

The invention claimed is:
1. A compound of formula

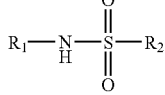

I wherein
$R_1$ is (methyl)(cyano)phenyl, (trifluoromethoxy)(cyano)phenyl, or (chloro)(cyano)phenyl, and
$R_2$ is chlorothienyl, bis-chlorothienyl, or (chloro)(bromo)thienyl.

2. A compound according to claim 1, selected from the group consisting of
5-Chloro-thiophene-2-sulfonic acid (4-cyano-2-methyl-phenyl)-amide,
4,5-Dichloro-thiophene-2-sulfonic acid (5-chloro-2-cyano-phenyl)-amide,
4,5-Dichloro-thiophene-2-sulfonic acid (4-cyano-2-trifluoromethoxy-phenyl)-amide, 4,5-Dichloro-thiophene-2-sulfonic acid (3-chloro-4-cyano-phenyl)-amide,
5-Chloro-thiophene-2-sulfonic acid (5-chloro-2-cyano-phenyl)-amide,
4-Bromo-2,5-dichloro-thiophene-3-sulfonic acid (4-cyano-2-trifluoromethoxy-phenyl)-amide,
4-Bromo-2,5-dichloro-thiophene-3-sulfonic acid (5-chloro-2-cyano-phenyl)-amide,
5-Chloro-thiophene-2-sulfonic acid (4-cyano-2-trifluoromethoxy-phenyl)-amide,
2,5-Dichloro-thiophene-3-sulfonic acid (4-cyano-2-trifluoromethoxy-phenyl)-amide, and
2,5-Dichloro-thiophene-3-sulfonic acid (5-chloro-2-cyano-phenyl)-amide.

3. A compound according to claim 1 in the form of a salt.

4. A pharmaceutical composition comprising a compound of claim 1 in association with at least one pharmaceutically acceptable excipient.

* * * * *